United States Patent [19]
Srinivasan

[11] Patent Number: 6,150,816
[45] Date of Patent: Nov. 21, 2000

[54] RADIO-FREQUENCY COIL ARRAY FOR RESONANCE ANALYSIS

[75] Inventor: Ravi Srinivasan, Richmond Heights, Ohio

[73] Assignee: Advanced Imaging Research, Inc., Cleveland, Ohio

[21] Appl. No.: 09/028,336

[22] Filed: Feb. 24, 1998

Related U.S. Application Data

[60] Provisional application No. 60/039,152, Feb. 25, 1997.

[51] Int. Cl.$^7$ .................................................. G01V 3/00
[52] U.S. Cl. ................................. 324/318; 324/322
[58] Field of Search .................... 324/318, 322, 324/321, 300, 314, 307, 309; 600/420, 421

[56] References Cited

U.S. PATENT DOCUMENTS

| | | | |
|---|---|---|---|
| 4,398,148 | 8/1983 | Barjhoux et al. | 324/307 |
| 4,411,270 | 10/1983 | Damadian | 128/653 |
| 4,692,705 | 9/1987 | Hayes | 324/318 |
| 4,769,605 | 9/1988 | Fox | 324/322 |
| 4,783,641 | 11/1988 | Hayes et al. | 333/219 |
| 4,793,356 | 12/1988 | Misic et al. | 128/653 |
| 4,799,016 | 1/1989 | Rezvani | 324/318 |
| 4,820,985 | 4/1989 | Eash | 324/318 |
| 4,825,162 | 4/1989 | Roemer et al. | 324/318 |
| 4,833,409 | 5/1989 | Eash | 324/318 |
| 4,943,775 | 7/1990 | Boskamp et al. | 324/322 |
| 5,057,778 | 10/1991 | Rath | 324/322 |
| 5,144,240 | 9/1992 | Mehdizadeh et al. | 324/318 |
| 5,194,811 | 3/1993 | Murphy-Boesch et al. | 324/322 |
| 5,202,635 | 4/1993 | Srinivasan et al. | 324/322 |
| 5,208,534 | 5/1993 | Okamoto et al. | 324/309 |
| 5,212,450 | 5/1993 | Murphy-Boesch et al. | 324/322 |
| 5,256,971 | 10/1993 | Boskamp | 324/318 |
| 5,258,717 | 11/1993 | Misic et al. | 324/318 |
| 5,270,656 | 12/1993 | Roberts et al. | 324/318 |
| 5,382,903 | 1/1995 | Young | 324/318 |
| 5,521,506 | 5/1996 | Misic et al. | 324/322 |
| 5,543,711 | 8/1996 | Srinivasan et al. | 324/318 |
| 5,548,218 | 8/1996 | Lu | 324/318 |
| 5,592,083 | 1/1997 | Magnuson et al. | 324/300 |
| 5,592,088 | 1/1997 | Matsunaga et al. | 324/318 |
| 5,594,338 | 1/1997 | Magnuson | 324/318 |
| 5,602,479 | 2/1997 | Srinivasan et al. | 324/318 |
| 5,646,531 | 7/1997 | Renz | 324/318 |
| 5,680,047 | 10/1997 | Srinivasan et al. | 324/318 |
| 5,777,474 | 7/1998 | Srinivasan | 324/318 |
| 5,917,324 | 6/1999 | Leussler | 324/318 |
| 5,999,000 | 12/1999 | Srinivasan | 324/318 |

OTHER PUBLICATIONS

Ravi Srinivasan and Haiying Liu, A Comprehensive Analysis for Estimating Modes in Coupled Resonators, p. 1425.
Michael Burl, Ian R, Young, Examples of the Design of Screened and Shielded RF Receiver Coils, pp. 326–330.
Srinivasan, Improved Radio–Frequency Coil and M Ethod for Resonance/Imaging Analysis, U.S. Patent Application No. 08/993,932, filed Dec. 18, 1997.
International Search Report related to PCT Patent Application No. PCT/US98/03529 dated Jul. 16, 1998.
"Optimized Birdcage Resonators for Simultaneous MRI of Head and Neck" by C. Leussler SMR 1993.
"A Comprehensive Analysis for Estimating Modes in Coupled Resonators"; by Ravi Srinivasan and Haiying Liu.
"Examples of the Design of Screened and Shielded RF Receiver Coils"; Michael Burl and Ian R. Young, pp. 326–330.

*Primary Examiner*—Louis Arana
*Attorney, Agent, or Firm*—Renner, Otto, Boisselle & Sklar LLP

[57] ABSTRACT

An RF coil array which includes first and second RF coils that are overlapped to eliminate their coupling (to maintain zero mutual inductance between them) through space, a third coil connecting the first and second coils such that there is no net coupling between the first two coils through the third coil, and in which all three coils are well isolated from one another at the resonance frequency or frequencies of interest.

33 Claims, 17 Drawing Sheets

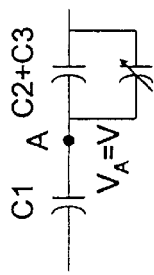
FIG. 7d
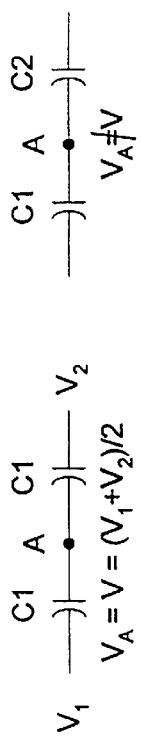
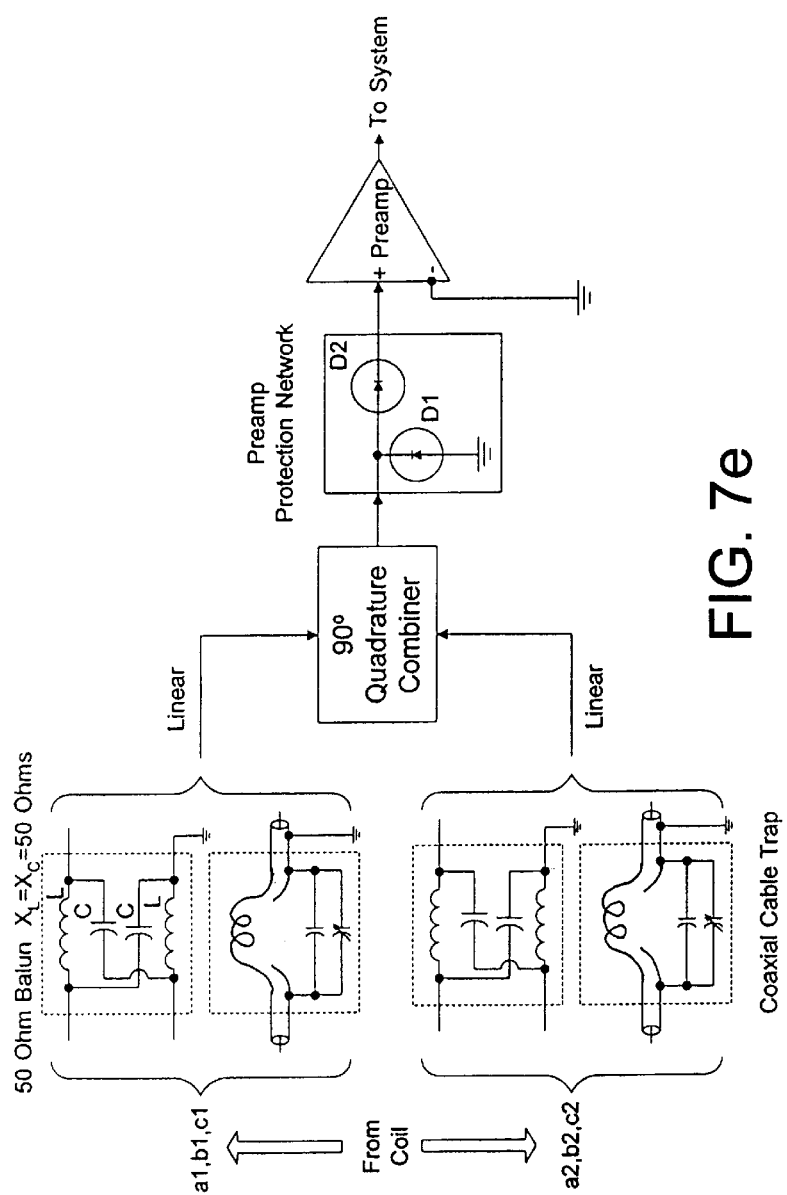
FIG. 7f
FIG. 7e

RADIO-FREQUENCY COIL ARRAY FOR RESONANCE ANALYSIS

This application is based on provisional application No. 60/039,152, filed Feb. 25, 1997, the entire disclosure of which is incorporated herein by reference.

TECHNICAL FIELD

The present invention relates to resonance systems, such as magnetic resonance imaging (MRI), nuclear quadrupole resonance (NQR), electron spin resonance (ESR) systems, and more particularly to a radio-frequency (RF) coil array and method for use in such systems.

BACKGROUND OF THE INVENTION

NMR or MRI

In MRI systems or nuclear magnetic resonance (NMR) systems, a static magnetic field $B_o$ is applied to the body under investigation to define an equilibrium axis of magnetic alignment in the region of the body under examination. An RF field is then applied in the region being examined in a direction orthogonal to the static field direction, to excite magnetic resonance in the region, and resulting RF signals are detected and processed. Generally, the resulting RF signals are detected by RF coil arrangements placed close to the body. See for example, U.S. Pat. No. 4,411,270 to Damadian and U.S. Pat. No. 4,793,356 to Misic et al. Typically, such RF coils are either surface type coils or volume type coils, depending on the particular application. Normally separate RF coils are used for excitation and detection, but the same coil or array of coils may be used for both purposes. For multiple surface RF coils for use in NMR, see U.S. Pat. No. 4,825,162 to Roemer, et al.

A further increase in S/N can be realized with the use of quadrature coils as compared to the conventional linear coil designs. See for example U.S. Pat. No. 4,467,282 to Siebold and U.S. Pat. No. 4,707,664 to Fehn. Also see U.S. Pat. Nos. 4,783,641 and 4,692,705 to Hayes for a quadrature volume coil, commonly referred to as the "birdcage" coil in the NMR community. For the use of multiple volume coils for use in NMR, see U.S. Pat. No. 5,258,717 to Misic, et al., and the reference article by Leussler for the use of multiple volume coils for simultaneous head and neck imaging (See, C. Leussler, "*Optimized Birdcage Resonators for Simultaneous MRI of Head and Neck*", SMRM 12th Annual Meeting, New York, Book of Abstracts, page 1349, 1993). Also, reference is made to commonly assigned U.S. patent application Ser. No. 08/745,893 filed on Nov. 8, 1996 titled "Radio-Frequency Coil and Method for Resonance Imaging/Analysis", and Ser. No. 08/993,932 entitled "Improved Radio-Frequency Coil and Method for Resonance Imaging/Analysis", filed on Dec. 18, 1997, the disclosures of which are incorporated herein by reference, for the use of multiple volume and surface coils for use in NMR imaging.

The recent introduction of array coils to NMR, has led to commercially available cervical-thoracic-lumbar (CTL) array coil for entire spine imaging, and flexible body arrays for torso imaging. These multichannel coils significantly help reduce scan times. A routine MR study takes approximately 45 minutes, including the patient placement. This is uncomfortable especially for claustrophobic patients in general. In addition, prolonged scan times make the contrast-enhanced studies even more difficult to obtain. The almost 1 hour MR study with and without the contrast agent makes MR not so suitable for imaging emergency trauma cases.

This necessitates a new array coil with high S/N, that will allow the MR study of the torso, head, spine or joints such as the knee, wrist and shoulder etc., to be performed in reduced scan times. This will significantly reduce patient discomfort and increase patient throughput in a MR scanner. The reduced scan times will also allow MRI systems to be used in scanning emergency trauma patients.

A new area of MRI namely functional MRI or more commonly referred to as fMRI has emerged in the recent years. This technique provides the capability of mapping the brain functions, non-invasively using MR. Unfortunately, a major drawback of this technique is its lack of sensitivity. Once again, a coil with improved S/N will provide a much clear image that will assist in the diagnosis of disorders in the human brain.

Nuclear Quadrupole Resonance (NQR)

NQR is a technique that is capable of locating and uniquely identifying nitrogen for the detection of explosives and/or narcotics, even when contained and concealed by other materials. NQR has potential application in general and medical imaging and industrial measurements, in addition to the detection of either explosives (including land mines) or narcotics. See U.S. Pat. Nos. 5,594,338 and 5,592,083 for the design of an RF coil employed in the NQR system.

Generally, a significant factor in contraband detection by means of NQR is that quadrapolar nuclei that are commonly present, and potentially readily observable, in narcotics and explosives include nitrogen ($^{14}N$) and chlorine ($^{35}Cl$ and $^{37}Cl$), among possible other nuclei. Thus, in commercial applications it is necessary to be able to detect quadrapolar nuclei contained within articles of mail, mail bags or airline baggage, including carry-on and checked luggage. The resonant frequencies of the nitrogen and chlorine in these substances are different for each chemical structure, but are well defined and remain consistent. That is, for a given chemical structure the resonance frequencies for nitrogen and chlorine compounds remain intact and do not change, unless their chemical structure is altered.

Generally, NQR frequencies of quadrapole nuclei lie within 0.5–5 MHz range. However, for organic chlorine compounds, $^{35}Cl$ chemical shifts range from 16–55 MHz. The chemical shift of chlorinated hydrocarbons occurs between 32–45 MHz. This is a very wide frequency range for one single turn RF coil of the aforementioned '338 and '083 references to cover.

Even the 0.5 to 5 MHz (a ten fold frequency) range of detection for $^{14}N$ in explosives and or narcotics mandate a capacitance of a factor of 100 ($f^2$ 1/LC) to tune the coil from 5 to 0.5 MHz range, which are overwhelmingly large range of capacitances required to tune the RF coil. Since, the same RF coil was used for a wide frequency range, the RF coil design was un-optimized for the several frequency ranges of operation. This may affect the performance of the RF coil (Q values) and the entire NQR system (transmitter power, S/N), in the detection of low levels of nitrogen compounds found in plastic explosives and narcotics.

This necessitates that the RF coil design be optimized for maximum S/N over at least a majority of the frequency ranges of NQR operation and detection in reduced examination times.

Distributed Type Volume Coils

Birdcage Coil

Even after several years following the introduction of array coils to NMR, the only coil that is commercially used for scanning the human head in a horizontally oriented $B_o$ magnetic field is the quadrature birdcage coil of Hayes '705. Other applications of this coil design are for the whole body, knee and wrist imaging. A birdcage coil consists of two rings connected by several straight segments referred to as legs. A planar schematic of an eight leg high-pass birdcage is shown in FIG. 1a. This coil consists of two end rings R1 and R2 and 8 legs 1 through 8. Each ring section between two legs are interrupted by two series 2C value capacitors. Their combined effect is one capacitor of C value. FIG. 1b is the front view of the birdcage describing the location of the ring with respect to the legs and includes the mode orientation. FIG. 1c is the side view of the coil outline shown for brevity.

The birdcage which is of the distributed inductance-capacitance type structure has several frequency modes. Of interest is the first or principal or k=1 quadrature mode. This k=1 quadrature mode has two linear components (1a, 1b), oriented orthogonal to one another as shown in FIG. 1b. As mentioned above, the quadrature coil provided a 41% improvement over the conventional linear coil designs. The birdcage expended half the power when compared to the conventional linear coil, thus significantly reduced the RF power deposited in the patient. The higher order or k>1 modes had no net field at the coil center and generally were not used for imaging. At the k=1 mode, the currents in the coil were cosinusoidally distributed such that the resultant field displayed a homogeneous distribution over the imaging field-of-view (FOV). It is for these regions this coil gained popularity in the NMR community for the several volumetric applications (torso, head, knee, wrist, etc.).

The dashed lines of FIGS. 1a, 1b and 1c are planes of symmetry for this birdcage. From FIG. 1b, there are four such planes (I, II, III, IV), that are distributed azimuthally (due to symmetry). There is one additional axial plane (V) that is centrally located between the two end rings R1 and R2, dissecting the coil axis (see FIG. 1c) which, in addition is also a virtual ground plane. The points where the planes of symmetry intersect the birdcage are "a, b, c, d, e, f, g, h" on ring R1 and "i, j, k, l, m, n, o, p" on ring R2, "q, r, s, t, u, v, w, x" on legs 1, 2, 3 . . . 8 respectively of FIG. 1a. Since points "q–x" are located on the virtual ground plane, these points are at virtual ground potential or have no net potential.

Should points "a–p" on the end rings be connected as shown in FIG. 1d, then the 8 leg coil of FIG. 1a will become a 16 leg coil of FIG. 1d and the frequency mode structure including the current distribution will be altered. The resultant structure in this case was still a single birdcage, even after the addition of eight more legs. Thus the increase in S/N was not realized even after this addition, although the homogeneity along the axial planes of the coil may have improved slightly over the eight leg coil. And since no increase in S/N was realized, this approach was unacceptable.

However, should the virtual ground points "q–x" in the legs of FIG. 1a be shorted, this will result in the coil of FIG. 1e. This will give rise to a new RF gradient mode, bi-phasic in nature with + & − lobes along the coil axis. However, it is noted that a RF gradient mode for the coil of FIG. 1e, has no net field at the coil center (i.e., the RF gradient mode has no net field in the central virtual ground plane of FIG. 1c). Therefore, although FIG. 1e has two birdcages that share one end ring $R_{12}$ and even a new mode is realized, no net increase in S/N at the coil center is realized.

3-Channel Distributed Type Coil Head Array

A quadrature, 3-channel head coil was described by the inventor in previously filed Ser. No. 08/993,932, which provided improved S/N at the coil center and toward the top of the head (see FIG. 2). The coil consisted of two birdcages (coils #1, #2), one distributed, quadrature modified surface coil (coil #3) and passive circuits were used for decoupling individual coils and to minimize the cross-talk between all coils in the array. The coil was operated in the multiple operating modes, with focus to the upper or lower portions of the brain or for routine head studies in one clinical setting, with high S/N and without compromising homogeneity. Here the birdcage, coil #2 and the quadrature surface coil #3 were asymmetrically overlapped and therefore isolated from one another and is the subject of previously filed U.S. Ser. No. 08/745,893.

The combination of coils #2 and #3 was then overlapped with birdcage coil #1. Since all three coils in the array were physically separated from one another, and were overlapped to maintain minimal mutual coupling, each coil in the array maintained their own RF current distribution and mode orientation. Several passive coil-to-coil decoupling electronics helped minimize the residual cross-talk between coils in the array. Each quadrature coil signal was routed to individual low noise figure, high gain preamplifiers before digitization. Diode protection circuits were inserted between the coil and the respective preamplifier for preamplifier protection during whole body transmit.

2-Channel Birdcage, Head and Neck Array

A quadrature, 2-channel birdcage array was described in C. Leussler, "*Optimized Birdcage Resonators for Simultaneous MRI of Head and Neck*", SMRM 12th Annual Meeting, New York, Book of Abstracts, page 1349, 1993 for simultaneous head and neck imaging (see FIG. 3). This coil involved 2 birdcages; a coil 10 for the head and a coil 12 for the neck. The head birdcage 10 had eight fold symmetry, whereas the neck birdcage 12 had only a four-fold symmetry. The neck birdcage 12 had shoulder cut-outs for accomodating the neck as shown in FIG. 3. This coil provided an extended FOV without significantly compromising S/N and homogeneity over the extended FOV. Nevertheless, no increase in S/N was realized over extended FOVs. That is, the S/N of the array coil was comparable to individual head or neck coils over the head & neck scan volume.

Distributed Type Surface Coils

The distributed surface coil of FIG. 4a has three meshes, 4 vertical segments referred to as legs and 2 horizontal segments referred to as ring segments. Each of the ring segments between the legs are broken with two 2C capacitors in series. Like wise, each of the end ring segments are also populated with two 2C value capacitors. For details of this coil design, refer to U.S. Pat. No. 4,783,641 to Hayes, et al.

The coil of FIG. 4a is of the high-pass configuration, and has three resonance modes. The principal or k=1 mode behaves like a simple loop coil of identical outside coil dimension of FIG. 4a (see FIG. 4b). The k=2 mode will behave similar to a butterfly design of FIG. 4c. Dashed lines I, II and III merely depict the mid voltage points "a–f" between 2 capacitors of identical values, whereas line IV is a virtual ground plane and points "g–j" are at virtual ground potential or have no net potential.

The main advantages of the distributed type coil designs are its distributed sinusoidal currents that help provide uniform B field distribution, and reduced losses. Also, the field profiles lay close to the coil which minimize tissue losses from the human body, thus increases coil S/N.

A multiple surface coil arrangement disclosed in U.S. Pat. No. 5,256,971 to Boskamp is shown in FIG. 4d. Here, two surface coils of similar dimension are overlapped for minimum mutual inductance from one another. A third coil is added to this set, such that the third coil is magnetically isolated from the first and second coils. Here, all three coils are mutually isolated from another. In doing so, the third coil has a different coil geometry than the first and second coils, and extends beyond the FOV of the first and second coils combined.

Should this arrangement of coils be flexed around the human torso, the isolation between the third coil and the first and second coils will change, which in turn will affect the isolation between the first and second coils, as the first and second coils will now start to couple via the third coil. That is, should the third coil begin to couple to either the first or second coils, all coils in the array will begin to couple with each other. This was not satisfactory.

This necessitates a coil system where the individual coils in the system are well isolated from one another and still maintain its current distribution and preferred mode orientation irrespective of its shape.

Single and Multiple Turn Solenoid Type Coils
Solenoid Coil for NMR

One of the oldest and perhaps the most popular coil design that is commercially utilized for the several volumetric applications ( torso, head, spine, knee, wrist) is of the solenoid design. See for example, U.S. Pat. No. 4,398,148 to Barjhoux et al.

FIG. 5a is one example of a solenoid head coil configuration commonly used in the NMR community. The N-turn solenoid is resonated with two series connected 2C value capacitors. This coil has 2 planes of symmetry, I and II, respectively. Plane I intersects the coil at virtual ground points "a , b". A side view of the coil outline along with the head and the central virtual ground plane I is shown in FIG. 5b, for brevity.

Shorting the two virtual ground points of FIG. 5a will result in FIG. 5c. This will give rise to a new RF gradient mode along the coil axis. It will be noted that a RF gradient mode has no net field at the coil center (i.e. the RF gradient mode has no net field in the central virtual ground plane of FIG. 5b). Therefore, although FIG. 4c has two solenoid coils sharing the two virtual ground point "a, b" of FIG. 5a and even a new gradient mode is realized, the homogeneous mode of FIG. 5a will not be affected and no net increase in S/N is realized at the coil center.

Single Turn Solenoid for NQR

A single turn solenoid coil of FIG. 6 was used to detect the $^{14}N$ signals in crystalline form for detecting concealed explosives and narcotics employing nuclear quadrupole resonance (NQR). See U.S. Pat. Nos. 5,594,338 and 5,592,083 for the design of an RF coil employed in the NQR system.

FIG. 6 has one single turn RF coil which is tuned to a wide range (approx 0.5 to 5 MHz), by simply adding large and small value capacitances for coarse and fine tuning with the help of relay switches. As seen, the upper frequency range was ten fold of the lower range which mandated a 100 fold change in capacitance to tuned the coil. Since, the same RF coil was used for a wide frequency range, the RF coil design was un-optimized for the several frequency ranges of operation. This may affect the performance (transmitter power, S/N) of the RF coil and the entire NQR system, in the detection of low levels of nitrogen and chlorine compounds found in plastic explosives and narcotics.

This necessitates that the RF coil design be optimized for at least a majority of the frequency ranges of NQR operation and detection which will also help in reducing examination times.

This RF coil design will allow for at least one optimized coil in the array that will cover a part of the frequency spectrum, such that all coils in the array combined cover the entire frequency spectrum required for detection. This will help reduce the overall scan frequency range per coil and thus allow rapid tuning of coils in the array. This RF coil design may also be designed to allow for multiple tuning of the coils in the array without crosstalk and capable of simultaneous operation, which will help scan the entire frequency range in reduced scan times.

It is therefore a primary objective of the present invention to further improve S/N and reduce scan times of all such coil systems used for resonance imaging or spectroscopic analysis mentioned above. Specific applications of the coil described herein in accordance with the present invention include distributed type surface and volume coils, and single and multiple turn solenoid type coils.

SUMMARY OF THE INVENTION

The present invention provides an RF coil with high signal-to-noise ratio (S/N) over the imaging or spectroscopic field-of-view (FOV). The RF coil of the present invention enables one to reduce scan times and therefore patient discomfort without significantly compromising image quality. The RF is capable of operating in different FOVs in the multiple operating modes in one or multiple frequencies. Furthermore, the present invention provides a coil array capable of simultaneous operation in at least one frequency range.

A primary objective of the present invention is to provide a novel RF coil design with high S/N, capable of array operation in the single or multiple frequencies. Another objective is to provide an array design, which will provide a high combined S/N than any one coil operated alone. Yet another objective is to provide a RF coil capable of simultaneous multiple frequency operation for resonance imaging/spectroscopic analysis. A further objective is to have coils in the array that are well isolated from one another and maintain their individual current distributions and mode orientations irrespective of the shape of the coil.

The design of the inventive coil involves first and second RF coils, that are overlapped to eliminate their magnetic coupling (to maintain zero mutual inductance between them) through space, a third coil physically connecting the first and second coils such that there is no net coupling between the first two coils through the third coil, and all three coils are well isolated from one another at the resonance frequency or frequencies of interest.

Please note all three coils in this coil system (first+second+third), may be volume type coils or surface type coils or a combination of both. A novel aspect of this invention is the unusual combination of coils in one integrated structure, that are well isolated from another and maintain their preferred current distributions and mode orientations.

In the embodiments of the present invention, the third coil has a FOV nearly identical to that of the combined FOV of the first two coils, and overlaps the combined FOV of the first two coils, such that, the S/N of all three coils combined is greater than any one coil operated alone. In other embodiments, several (first+second+third=integrated) such integrated coils are overlapped for minimal mutual inductance and used in an array configuration. The three individual coils in any one integrated design may be tuned to one or more resonance frequencies, for simultaneous use in imaging or spectroscopic analysis. Depending on the imaging FOV, individual coils in the array can be turned OFF or ON by the programmable transmit/receive (T/R) driver in the resonance system.

According to one particular aspect of the invention, a radio-frequency (RF) coil array for resonance imaging/ analysis is provided. The coil array includes a first RF coil sensitive to RF signals produced during resonance imaging/analysis; a second RF coil located relative to the first RF coil with substantially zero coupling therebetween at a frequency or frequencies of the RF signals; and a third RF coil located relative to the first RF coil and the second RF coil such that there is substantially zero net current flow between the first RF coil and the second RF coil via the third RF coil, each of the first RF coil, second RF coil and third RF coil being substantially isolated from the other coils at the frequency or frequencies of the RF signals.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 1b is a is a schematic end view of the birdcage coil of FIG. 1a;

FIG. 1d is a planar schematic of a modified birdcage coil of FIG. 1a;

FIG. 1e is a planar schematic of a modified birdcage coil of FIG. 1a;

FIGS. 4b and 4c represent the principal and secondary modes, respectively, for the coil of FIG. 4a;

FIG. 5b is a side view of the coil outline of FIG. 5a;

FIG. 5c is a modified version of the coil of FIG. 5a;

FIG. 7d is a schematic view of exemplary isolation circuits in accordance with the present invention;

FIG. 7e is a schematic view of an exemplary coupling mechanism in accordance with the present invention;

FIG. 7f is a table illustrating various combinations of individual coils for different modes of operation in accordance with the present invention;

FIG. 8b is a schematic front view of the coil array of FIG. 8a;

FIG. 8c is a side view of the coil outlines of the array of FIG. 8a;

FIG. 11b is a front view of the coil array of FIG. 11a;

DESCRIPTION OF THE PREFERRED EMBODIMENTS

Figure 1A:
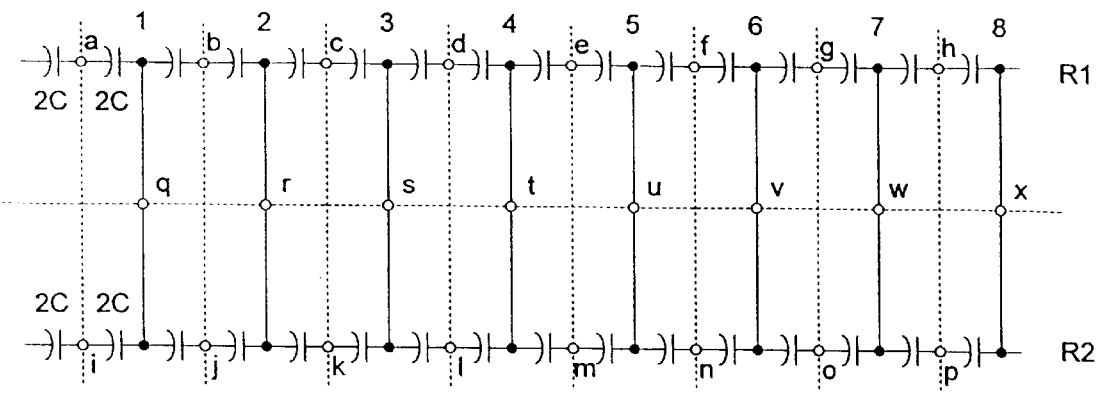
FIG. 1a is a planar schematic view of a high-pass birdcage coil.
Figure 1B:
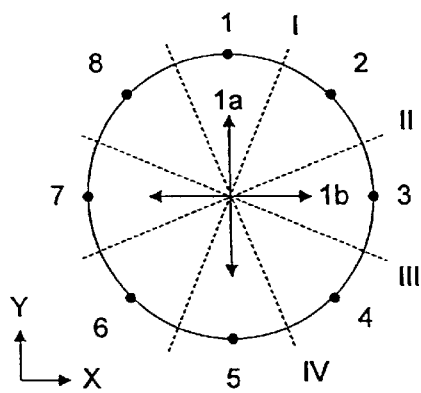
Figure 1C:
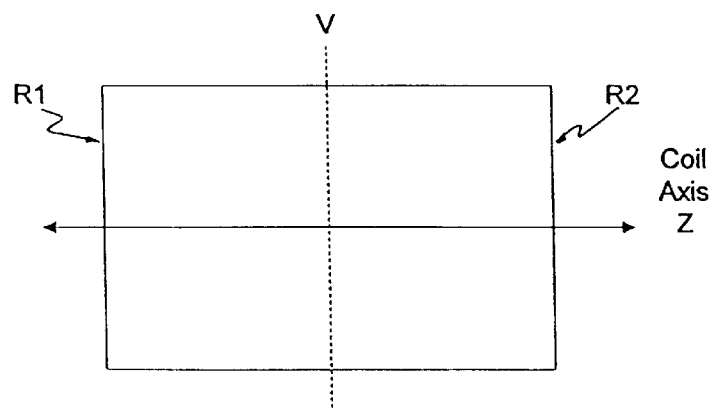
FIG. 1c is a side schematic view of the birdcage coil of FIG. 1a illustrating the plane of symmetry.
Figure 1D:
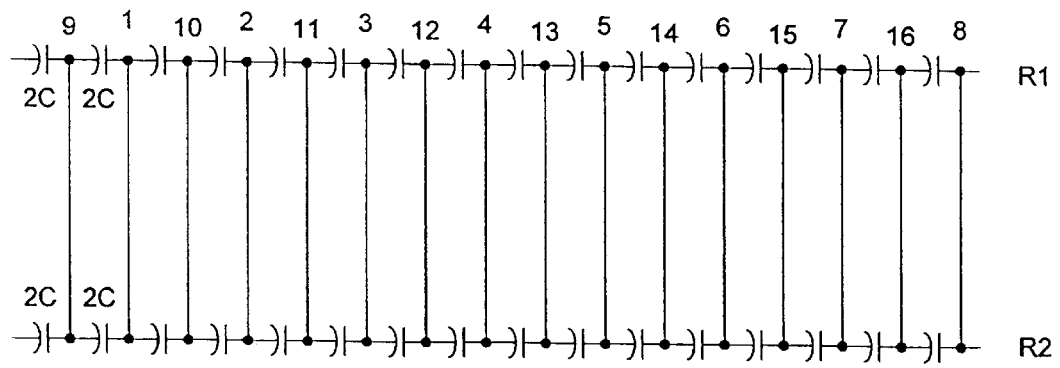
Figure 1E:
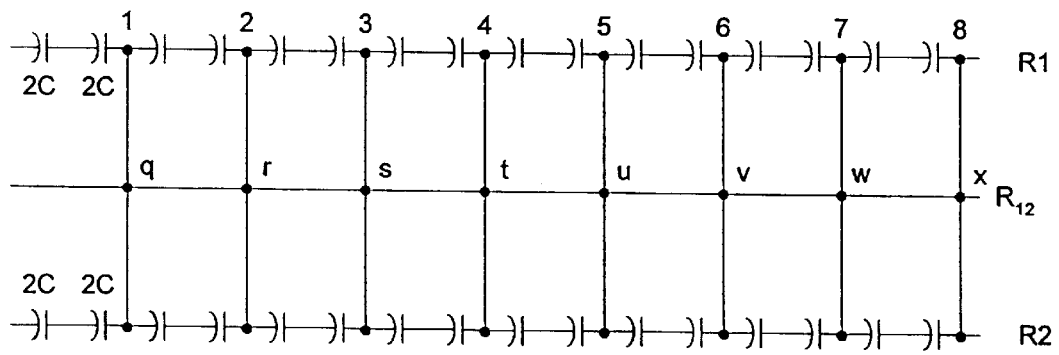

The present invention will now be described with reference to the drawings wherein like reference numerals are used to refer to like elements throughout.

Figure 7A:
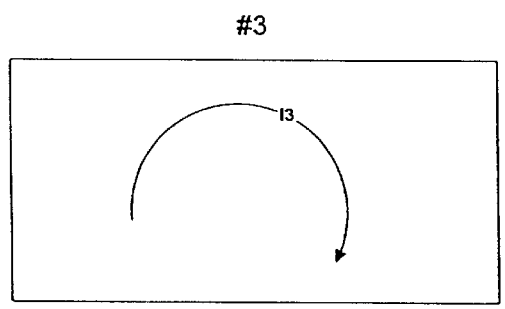
FIG. 7a is a simplified illustration of a coil array in accordance with the present invention in which three coils are shown with respective current distributions.
Figure 7A:
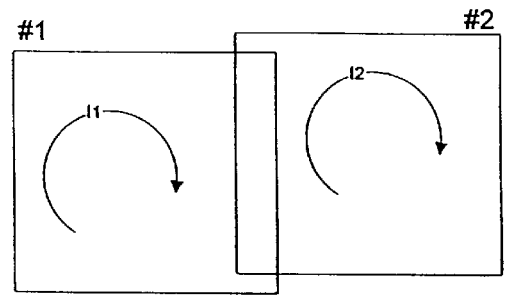

Referring initially to FIG. 7a, the invention includes first (coil #1) and second (coil #2) RF coils, that are overlapped to isolate the coils from each other, by causing the net shared flux between the coils to be zero. A third RF coil (coil #3) of FIG. 7a, is superimposed on the combination of coils #1 and #2, and physically connects coils #1 and #2 at several points along the coil periphery (see FIG. 7b). For the sake of explanation, the coil #3 may connect to coils #1 & #2 at points A, B and A', B' respectively. This however is done such that there is no net coupling between coils #1 and #2 through coil #3. Thus coils #1 and #2 are isolated from one another and still maintain their individual current distributions and B field orientations. Also, the currents in coil #3 are undisturbed and maintain their original distribution and B field orientation. Thus, all three coils are well isolated from one another and perform the intended function in a resonance experiment independent of the other.

Only coil outlines are shown in FIG. 7a for brevity. Not shown are impedances (inductances & capacitances) needed to resonate the RF coil at the frequencies of interest. It will be appreciated that the individual coils of FIGS. 7a may be of the volume type or the surface type or their combination as is discussed more fully below in connection with the specific embodiments.

Individual current distributions of coils #1, #2 and #3 are shown in FIG. 7a. Accordingly, their resultant B field orientations are directed in to the plane of the paper (if the fingers of the right hand are curled in the direction of the current, according to the right hand rule, the resultant B field direction of the coil is in the direction of the thumb, and in this case will be pointing in to the plane of the paper). By way of overlapping coils #1 and #2 are isolated from one another and maintain their individual current directions and preferred mode orientations. Here mode is referred to as the frequency mode of interest for a resonance experiment. For the cases of NMR or NQR, the modes of interest may be for one or more distinct radio-frequencies. However, mode orientations are the orientations of the B field over the imaging or the spectroscopic field-of-view (FOV) for individual RF coils, at the frequencies of interest. That is, for a linear RF coil case, there exists one mode that is of interest and one mode orientation. However, for a quadrature RF coil case, there exists two linear modes that are oriented orthogonal to one another. These two linear modes however may be tuned to the same frequency resulting in a quadrature coil, or may be tuned to two distinct frequencies thus depicting a dual tuned RF coil with linear operation at both frequencies.

Although it is preferred that coils #1 and #2 maintain identical coil dimensions, it is not an absolute necessity. In fact included in this disclosure is a head and neck array, where coils #1 and #2 are not identical in dimension. Nevertheless for the sake of simplicity, coils #1 and #2 of FIG. 7b have identical dimensions. Coil #3 connected to this combination of coils #1 and #2, encompasses a larger FOV covered by coil #1 or #2 alone. In fact, the FOV of coil #3 in this case is not only comparable but also superimposes the combined FOV of coils #1 and #2.

The combined S/N of coils #1 and #2, at the coil center (at the region of overlap) may be close or equal to the S/N of coil #3 of FIG. 7a. Thus the combined S/N of all three coils, that are isolated from another will be substantially greater than any one coil in the array. This is because the direction of currents in all three coils will remain the same and have similar B field orientations. Hence signals from all three coils add up. Since they are isolated from one another the noises from the coils in the array are uncorrelated, resulting in a substantial increase in combined S/N. For details of the mathematical expressions of combined S/N, refer to equations 19 and 20 of U.S. Pat. No. 4,825,162 of Roemer et al.

Coil Optimization Procedure

Since the inventive design has three coils in one integrated system, all coils must be isolated from one another to reduce their cross-talk which is necessary to increase the combined S/N of an experiment. In order to cancel the magnetic coupling between neighboring coils, they must be overlapped to cancel their net shared flux. The flow chart of FIG. 7c, represents a procedure suitable for optimizing all coils in the integrated coil system of FIG. 7b.

In steps S1 and S2, the first coil #1 is built and tested individually. Next, in step S3 the second coil #2 is built. In step S4, coil #1 and #2 are overlapped to cancel their coupling. Namely, in step S5 it is determined whether coils #1 and #2 are isolated by a predefined acceptable amount (e.g., coupled by less than −20 dB). If no in step S5, the coils #1 and #2 are repositioned relative to each other in an effort to improve the isolation therebetween. Steps S4 and S5 can then be carried out until acceptable isolation is achieved. If yes in step S5, the combined coils #1 and #2 may be tested as represented in step S6.

Then coil #3 will be built and added to this assembly as represented in step S7. After this addition, should the isolation between coils #1 & #2 deteriorate as determined in step S8, then either coils #1 & #2 be overlapped to compensate for the cross-talk introduced by the addition of coil #3 or the mechanism of FIG. 7d be used or a combination of both can be used to reisolate coils #1 & #2 after the addition of coil #3. (Step S9). Overlapping coils #1 & #2 again will cancel the net mutual flux shared by coils #1 & #2 after the introduction of coil #3. Final testing of the assembled array can then be carried out in step S10 upon achieving acceptable isolation between the respective coils. Once this optimum overlap is determined, a relatively high precision of duplication can be achieved from one coil batch to another in mass production, by etching the two coils on one or both sides of a single printed circuit board. However in addition to the above, any cross-talk by way of current flow between coils #1 & #2 via coil #3 can be minimized or eliminated in some instances by following the mechanism of FIG. 7d. Furthermore, if there exists any residual cross-talk, this too can be minimized or eliminated by introducing electrical coupling cancellation networks, one example may be similar to that of U.S. Pat. No. 4,769,605 to Fox.

Figure 7B:
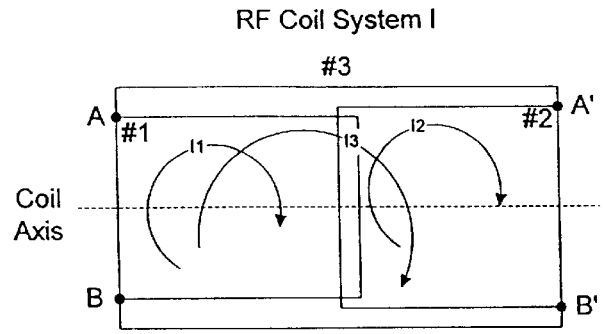
FIG. 7b is a schematic illustration of the coil in accordance with the present invention.
Figure 7C:
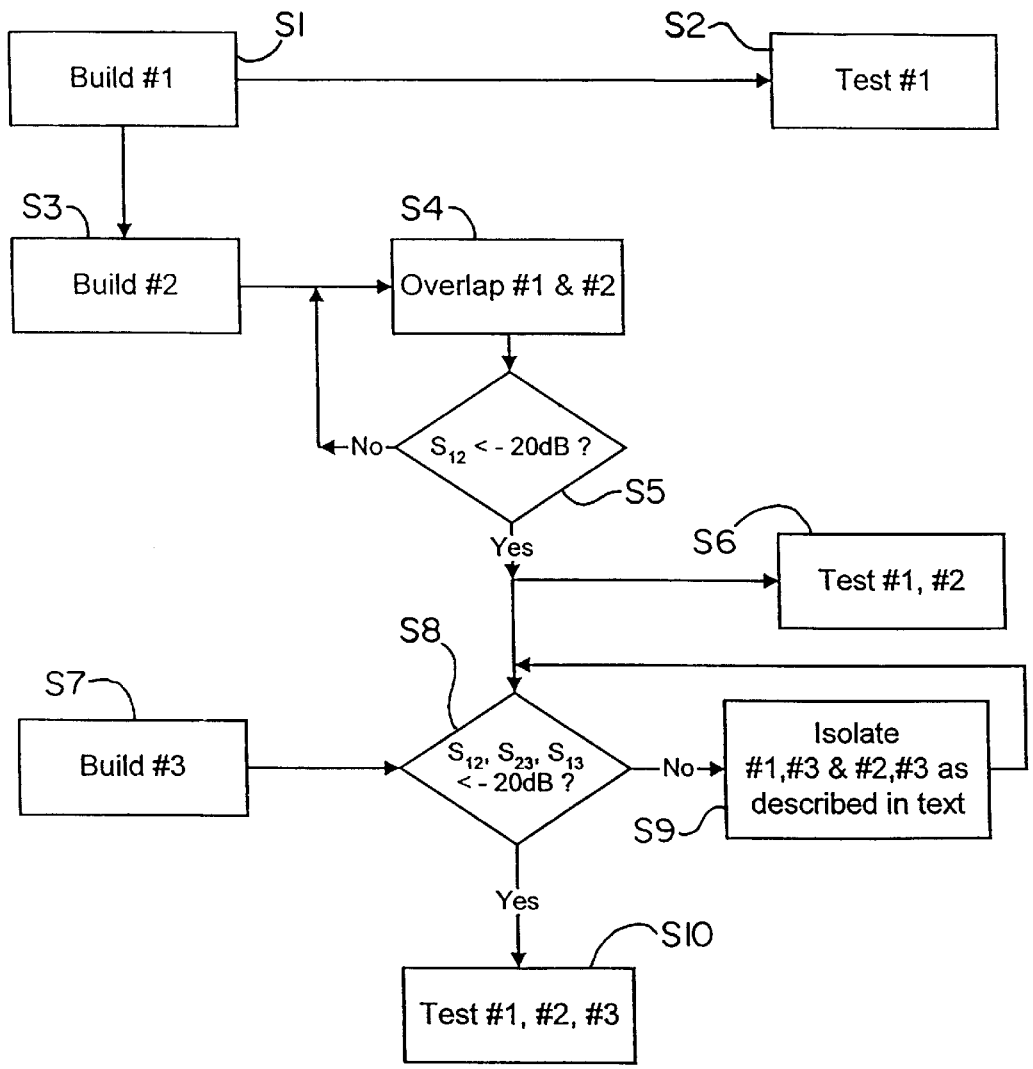
FIG. 7c is a flowchart representing exemplary steps for manufacturing a coil array in accordance with the present invention.

It will be appreciated that FIG. 7c represents exemplary steps, many of which are optional. For example, the testing of the coils in steps S2 and S6 may be omitted in view of only final testing in step S10.

From FIG. 7b, coil #3 connects to coils #1 & #2 at points A, B & A', B', respectively. If points A, B & A', B' were mid-points between two identical capacitors, then their voltage will be an average of the two potentials spanned by the two identical capacitors. This average potential may be denoted as being equal to V. In the present case, when coils #1 & #2 are identical, points A & A' in coils #1 & #2 will be at equi-potential. Similarly, points B & B' will also be at equi-potential. Please note, points B & B' may or may not be at the same potential as points A & A', which will depend on either the coil symmetry, or the distrubution of impedances within the coil or a combination of both. Since there will be no current flow between points of equi-potential, there is not net coupling between coils #1 & #2 via coil #3 with its addition. That is, the isolation between coils #1 & #2 will remain virtually the same with or without the addition of coil #3. Note, this will be true only if the net flux shared by coils #1 & #2 are close to zero or the cross-talk between them is almost negligible or both the above conditions are satisfied, before the adddition of coil #3.

For example (see FIG. 7d), let V1 and V2 be the voltages spanned by the two identical capacitors C1, then point A midway between V1 & V2 will be at a potential $V_A = V = (V1+V2)/2$. In reality, this is an ideal case where the two capacitors are identical in value. However, since 5% tolerance capacitors are generally used in manufacturing, point A may not always be at potential V. Here, point A can be forced to be at potential V by adding or taking away some capacitance value thereby balancing the potential across the capacitors and forcing the points mid-way between them to be at their average values. In the cases where all coils are etched on to a printed circuit board, then the capacitances on the coil can be slightly altered with the addition or subtraction of either small value fixed or trimmer capacitors across C1 and C2 to isolate the coils in the array.

For example in FIG. 7d, lets say C2 has 10% less capacitance than C1, then C2 will have greater potential drop across it than C1 (since, potential drop across C is equal to $I/j\omega C$, I is the current, $\omega$ is equal to $2\pi f$, f is the frequency of operation) and therefore point "A" will be at some potential other than at V. But this could be easily corrected by either adding small value fixed capacitors or trimmer capacitors across C2 such that C1=C2+C3 and will have the same potential drops across them. Now, this will force point "A" to be at the average of potentials V1 & V2 spanned by the capacitors. Likewise, some capacitance can be taken away if the capacitance values were greater.

It is by these ways (cancelling net mutual shared flux or isolating with any other scheme, proposed additional isolation scheme of FIG. 7d and/or that of Fox, with the above) the isolation between the above coils can be maintained if all coils were fixed or etched on a rigid or on a flexible printed circuit board. Note, an isolation of −20 dB was set as a target. In actuality, this value can be set to any other number based on the coil design and expected combined S/N. We set a −20 dB value, as this will relate to a 1% loss in combined S/N from the optimum value obtained at coil overlap for coils of identical dimension. For details of coil isolation values and its relation to S/N, please refer to the article by Tropp et al., in the Review of Scientific Instrumentation, Volume 62, Number 11, November 1991.

Finally, although it is advantageous to test the individual coils separately as they are built (like that shown in FIG. 7c), once the optimum settings of the coils and isolation values are engineered and specifications met, then simply final testing of the entire RF coil system (consisting of coils #1, #2 and #3) is advised. This will considerably cut the time and costs incurred in the final production line prior to product shipment. However, the proposed flow-chart is a methodical progression of the coil design which is also designed so to enable a relatively easier debugging or trouble shooting of the coil system when needed.

Individual Coil Coupling

A preferred method of coupling to individual coils in the RF coil array and interfacing to the system is shown in FIG. 7e. Let us assume the case when all coils in the array of FIG. 7b are in quadrature. Then there will be a total of six linear modes, operating at the resonance frequency of interest. These modes are a1 & a2 of coil #1, b1 & b2 of coil #2 and c1 & c2 of coil #3, respectively.

Generally, the linear modes of a coil are matched to 50 ohms using balanced matched capacitors (not shown) and connected to quadrature hybrids via baluns. Either 50 ohm "criss-cross" discrete network ($X_L=X_C=50$ ohms; L=124nH, C=50 pF for approx. 64 MHz or 1.5 T) or shielded, transmission line networks such as coaxial cable traps tuned to frequencies very close to the resonance frequency may be used as baluns to convert the balanced feed to an unbalanced line (see FIG. 7e). This is done to isolate the coil grounds from the system ground and to prevent leakage of the circulating RF currents on the ground shield of the coaxial cable exitting the system.

These networks (discrete or transmission line) are shielded as shown by the dotted lines to minimize their interaction with the whole body transmit field and their interaction with the RF coils themselves. Note, it is not necessary to shield the discrete networks but are shown as the preferred embodiment. However, we prefer that the cable traps be shielded so the fields generated by the traps are contained to within the volume encompassed by their shield. This is also done so the cable trap can be made uni or bi directional, depending the nature of the trap's use. The cable trap shown can be made uni directional by shorting its shield to one side of the coaxial cable shield. Likewise it can be made bi-directional by floating the shield, as shown in FIG. 7e.

The cable trap consists of two turns 1" in diameter, is wound on a delrin spindle with groves, using a semi-rigid cable of 0.085" o.d. along with fixed and variable capacitors for tuning a specified frequency range centered around the resonance frequency of operation. The RF shield is approximately 1.5×1.5×0.5" in dimension. With inductor Q values (of that of L in the discrete or that created by the coaxial cable in the transmission line network) of approximately 175–200, impedances (with zero reactances=resistance) of approximately 8–12K$\Omega$ can be realized across the baluns, which is adequate to isolate the grounds at 64 MHz (Resistance R=Q$\omega$L). Thus coil to ground leakage and coil to coil interactions be minimized or eliminated and high RF coil efficiencies can be maintained.

Then the linear signals are combined using a phase shifting network to create a single quadrature output per coil. This is followed by a diode protection network before the preamplifier. All three coils are actively decoupled during whole body transmit (circuitry not shown). Although this decoupling will achieve a−25 dB isolation per coil at the resonance frequency of operation, the additional series-shunt pin-diode protection circuit shown will provide a further −45 dB of isolation between the coil and the preamplifier in every channel. During whole body transmit, diode D1 is turned ON which shunts all the RF present in the signal line to ground before reaching the preamp. Diode D2 is reverse biased during transmit and helps further isolate the RF present in the signal conductor to the preamp input. During receive D1 is reverse biased and D1 is forward biased to allow all of the RF signals to the preamplifier before digitization and further amplification at the system receiver. Thus the diode circuit will ensure a safe preamp operation (preamp input maximum of roughly +20 dBm).

Thus all 3 coils are interfaced to 3 channels in a resonance receiving system. It is to be noted, that this way of interfacing the coils to the system is preferred. However, the outputs from the individual coils can be further combined and interfaced to fewer channels of the resonance system. For example, the quadrature outputs from coils #1 & #2 or from all coils #1, #2 & #3 can be combined prior to interfacing to the system, the latter case resulting eventually in a single channel. Likewise, individual modes from all coils can be interfaced to their respective channels (in this case six channels, two from each coil) of the transceiver of a resonance system.

Mode of Operation

Regardless of the frequency of operation, please note the individual coils of FIG. 7b can be turned ON or OFF using the programmable T/R drivers of the resonance system which will result in a total of 7 modes of operation for this 3 coil network, as shown in FIG. 7f.

For example in one configuration, coils #1 and #2 are turned ON and coil #3 is turned OFF. Likewise, coil #1 is turned ON and coils #2 and #3 are turned OFF. All such combination of coils are shown in FIG. 7f. Only two such combinations currently seem not possible, where coil #3 is ON and coil #1 is ON (coil #2 turned OFF) or where coil #3 is ON and coil #2 is ON (coil#1 turned OFF). This is because if one of two coils #1 or #2 are turned OFF, then coil #3 will couple to coils #2 and #1, respectively through space since the minimum mutual inductance condition was not achieved between them. However, it should be understood that one skilled in the art can counteract this unwanted coupling with the addition of electrical cancelling networks or some modification of the coils themselves or a combination of both.

RF Coil System Arrays

Figure 7G:
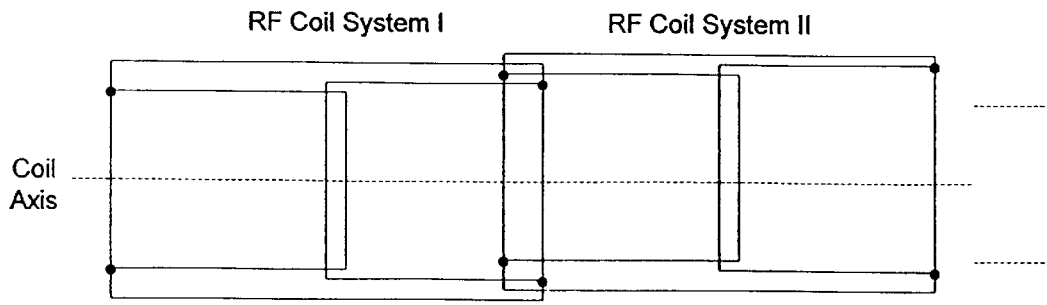
FIG. 7g is a schematic illustration of a plurality of coils in combination in accordance with the present invention.

Finally, several of these integrated (coil #1+coil #2+coil #3) coil systems, may be overlapped to provide high combined S/N over extended FOVs, as shown in FIG. 7g.

In summary, coils #1, #2 and #3 may be linear or quadrature and of the volume type or surface type or their combination. Should the coils be of the volume type, the dashed line of FIG. 7b will be along the common coil axis. Also, the coils may be tuned to the same or different resonance frequencies. For example, coils #1, #2 and #3 may be tuned to the same resonance frequency. In an another example, coils #1 and #2 may be tuned to one resonance frequency, and coil #3 is tuned to another resonance frequency. In yet another example, the individual coils in the array are tuned to different resonance frequencies and capable of simultaneous operation.

A few examples of the above concept are extended to distributed type volume coils like the birdcage, distributed surface coils and solenoid type coils. Their specific applications to NMR and NQR are described as embodiments of the present invention disclosure.

| Embodiment # | Type | Description | Application |
|---|---|---|---|
| 1. | Preferred embodiment described above | | |
| 2. | Volume | Birdcage | NMR - for brain imaging |
| 3. | Volume | Birdcage | NMR - for brain imaging |
| 4. | Volume | Birdcage | NMR - for knee imaging |
| 5. | Volume | Birdcage | NMR - for wrist imaging |
| 6. | Volume | Birdcage | NMR - for head and neck imaging |
| 7. | Surface | Distributed | NMR - for spine or torso imaging |
| 8. | Volume | Solenoid | NMR - for brain, knee, knee, elbow, wrist, foot or ankle, torso NQR - security checks for detection of narcotics, plastic explosives, etc. |

Embodiment #2—3 Channel, Quadrature Birdcage Array

Figure 8A:
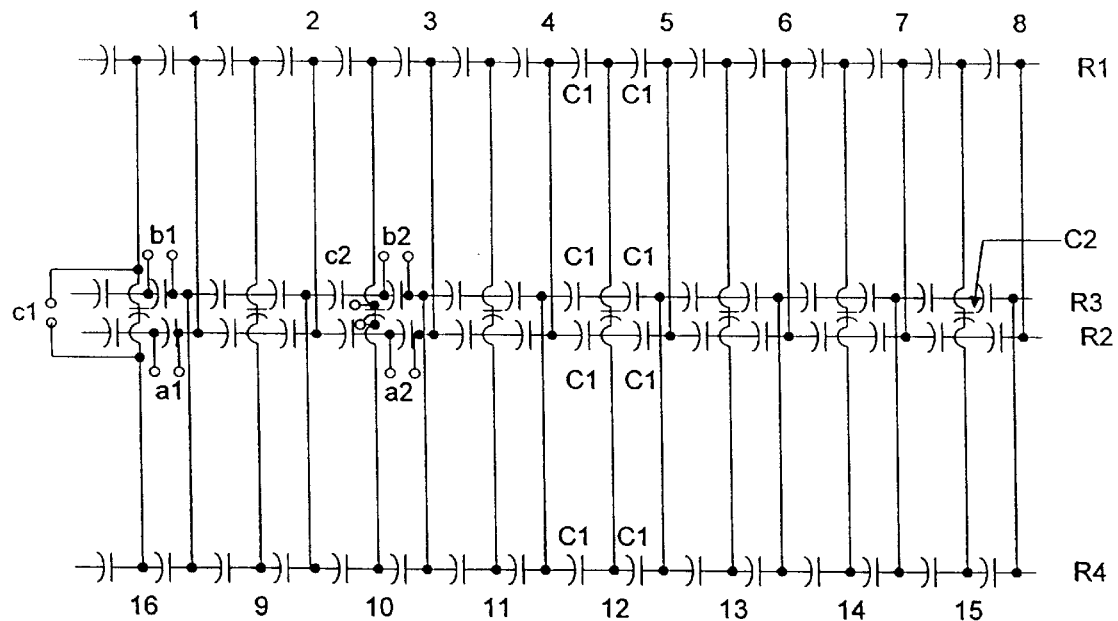
FIG. 8a is a planar schematic view of another embodiment of the coil array in accordance with the present invention.

Embodiment #2 of this invention is the receive only coil of FIG. 8a. This consists of two birdcages (#1, #2) overlapped to maintain minimum mutual inductance, such that the net flux shared by them is zero. Coil #1 consists of rings R1, R2 and eight legs (1,2,3 . . . 8) that connect them. This coil is resonated with C1 value capacitors. Coil #2 consists of R3 and R4 and eight legs that connect them and are also resonated with C1 value capacitors. Note, the 8 legs of coil #2 are co-linear to that of coil #1. Here, both coils #1 and #2 are identical in dimension. Coil #3 connects coil #1 and #2 at 16 points. Coil #3 comprises of rings R1 and R4 which are connected by eight legs (9, 10, . . . 16). Coil #3 is resonant with C1 and C2 value capacitors. All coils are tuned to the same resonance frequency of interest.

After the addition of C2 to coil #3, the isolation between coils #1 and #2 remained virtually the same, which means that the eight legs of coil #3 intercepted rings R1 and R4 at corresponding equi-potential points. In this particular case, the eight legs of coils #1 and #2 happened to be at the symmetry planes for coil #3. Thus there was no net coupling between coil #1 and #2 via coil #3. There was also no net coupling between coil #3 and coils #1 or #2. Thus each coils maintained their own current distribution and their own mode distributions.

Figure 8B:
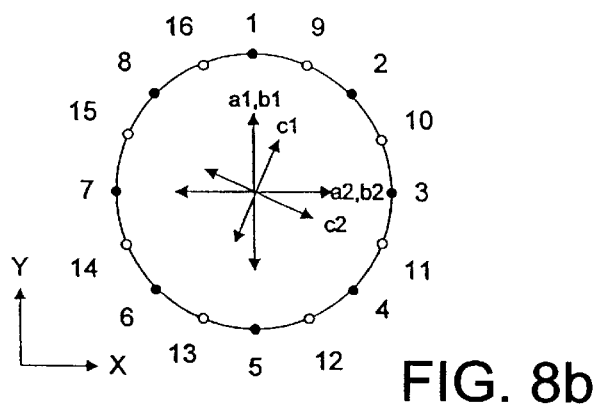

FIG. 8b is a front view of the coil, and shows the location of the legs of the birdcage and their mode orientations of the six linear modes of coils #1, #2 & #3 (a1, a2, a3, b1, b2, b3). Closed dark dots are locations of the legs of coils #1 & #2 connecting end rings R1 & R3 to R2 & R4 respectively, whereas open circles are for coil #3 which connect to end rings R1 and R4 only.

Figure 8C:
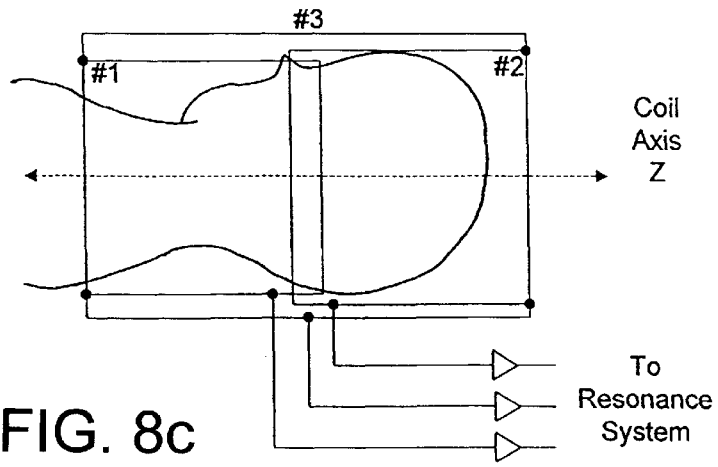

FIG. 8c is a side view of the coil outlines, with a head cartoon. As seen, coil #1 coverage extends from the c2–c3 cervical-spine and extends to the top of the cerebellum, coil #2 coverage extends from the mid cerebellum to the top of the head, whereas coil #3 coverage spans the combined FOV's of coils #1 & #2, respectively. Thus, routine head scanning can be accomplished with enhanced S/N, which can be used to reduce scan time or enhance image resolution or a little bit of both can be accomplished with the inventive coil. Furthermore, where specific focus is needed, either coil #1 or coil #2 can be individually turned ON to scan different portions of the human brain. Coupling to the six linear modes of this coil and their interface to the system can be accomplished similar to FIG. 7e. Here, three quadrature coil outputs are interfaced to 3 channels of a NMR system.

Embodiment #3—4 Channel, Quadrature Head Array

Figure 2:
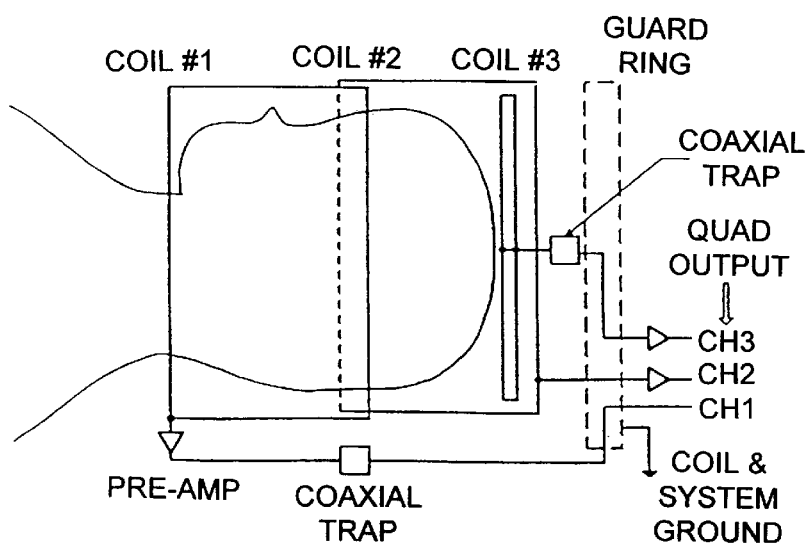
FIG. 2 is a schematic view of an RF coil having two birdcage coils, and modified spoke type quadrature surface coil.
Figure 8D:
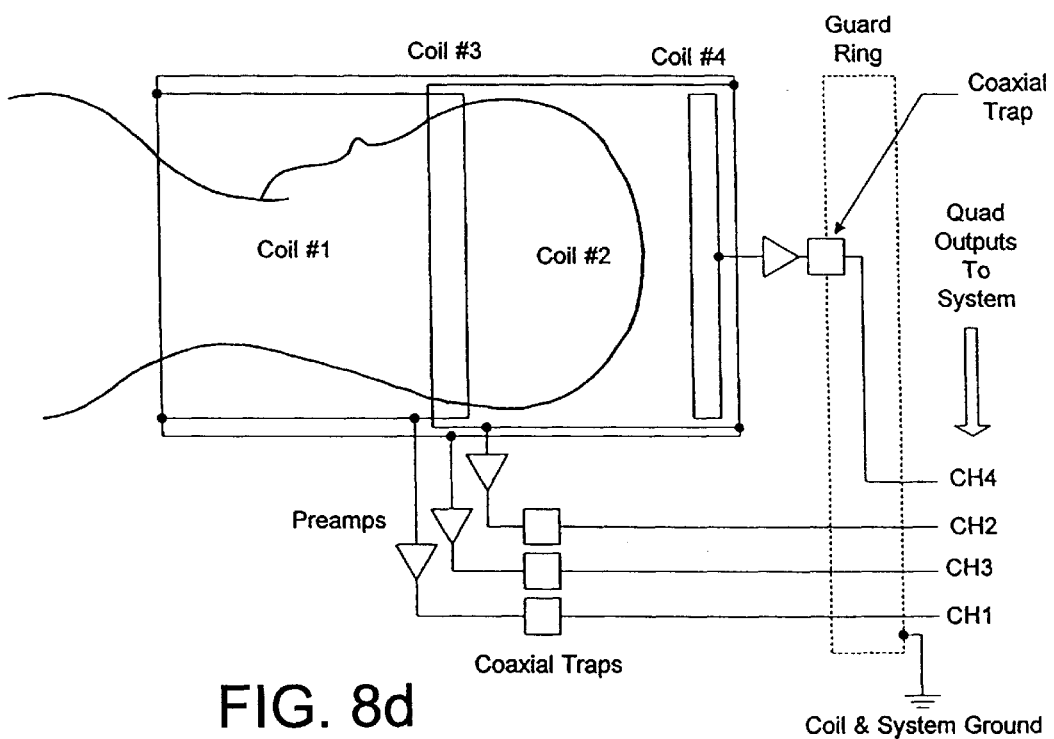
FIG. 8d is a schematic view of a 4-channel, quadrature head array in accordance with the present invention.

A quadrature, 3 channel head coil was described by the author of this invention in the previously mentioned application Ser. No. 08/993,932. See FIG. 2 for details. The S/N of this prior art coil can be further improved over the entire brain with the addition of coil #3, of FIG. 8d. This is also similar to adding coil #4 in FIG. 8c, needed to provide improved S/N over regions in the top of the head.

Coils #1, #2 and #3 have eight legs. Coil #4 is of the self-shielded type and has a total of 16 legs (8 primary and 8 secondary). See the above-mentions application Ser. Nos. 08/745,893 and 08/993,932 for the details of the coil #4's design and construction. Each of the four quadrature outputs from the coils in the head array are interfaced to 4 channels of the resonance receiving system, in this case a NMR receiving system. Please note, all four coils have a shielded, tuned coaxial cable trap in addition to the coupling and interface electronics mentioned in FIG. 7e. These coaxial cable traps help further isolate the RF coil grounds at the preamplifier level to the system ground and interfaces the coil outputs to the system receiver.

Please note, individual coils in the array can be turned ON or OFF to image a smaller FOV than the entire coil. If the focus was on the upper parts of the brain, only coils #2 and #4 need be turned ON, whereas if the focus was on the mandible areas only coil #1 may be turned ON.

Embodiment #4—3 Channel, Quadrature Knee Array

Figure 9A:
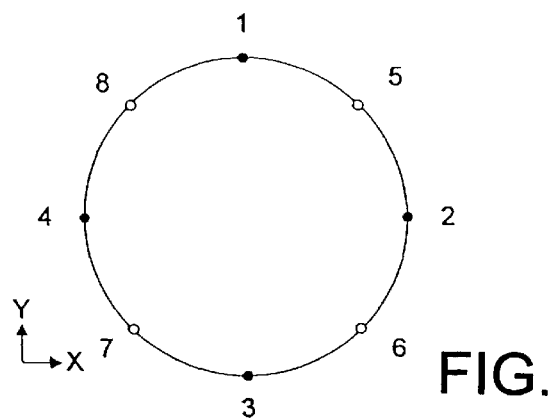
FIGS. 9a and 9b are front and side views of a 3-channel, quadrature knee array embodiment in accordance with the present invention.
Figure 9B:
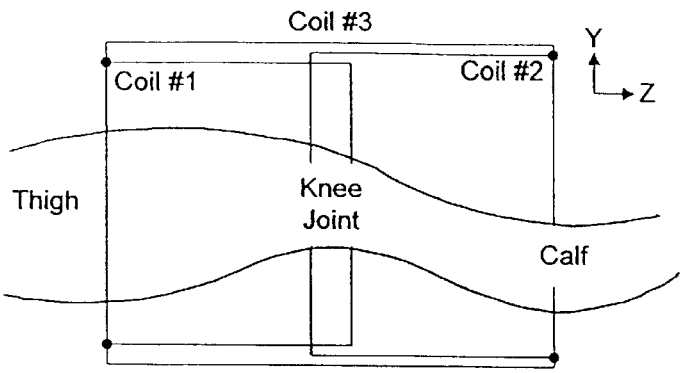

FIG. 9a and 9b are front and side views showing the coil outlines of the knee array. Here, coils #1, #2 and #3 have 4 legs, each. Legs 1, 2, 3 and 4 belong to coils #1 and #2 while 5, 6, 7 and 8 belong to coil #3. All legs are azimuthally distributed as shown in FIG. 9a. Coils #1 and #2 are first overlapped to maintain minimum mutual inductance. Coil #3 is then added which physically connects to coils #1 and #2, such that there is no net coupling between coil #1 and #2 via coil #3. A side view of the coil outlines along with a knee cartoon is shown in FIG. 9b.

Figure 9C:
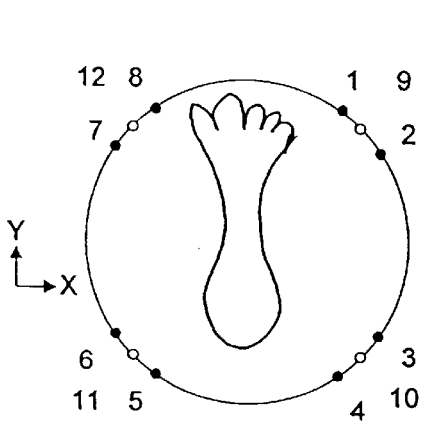
FIG. 9c schematically represents a modified knee array in accordance with the present invention.

FIG. 9c is a modified knee array. Here, coils #1 and #2 have 8 legs (1,2,3 . . . 8) each, distributed in the fashion shown. These coils are first overlapped to maintain minimum mutual inductance. Coil #3 that physically connects coils #1 and #2 have only 4 legs (9,10,11,12) which are distributed symmetrically. This arrangement is done to image the foot and the ankle along in addition to imaging the knee and the human calf. Please note, the coils of FIGS. 9 may have a split-top to ease the patient access.

Embodiment #5—3 Channel, Quadrature Wrist Array

Figure 10A:
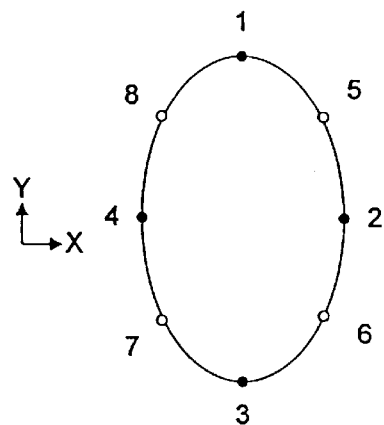
FIGS. 10a and 10b are, respectively, schematic front and side views of a 3-channel, quadrature wrist array in accordance with the present invention.
Figure 10B:
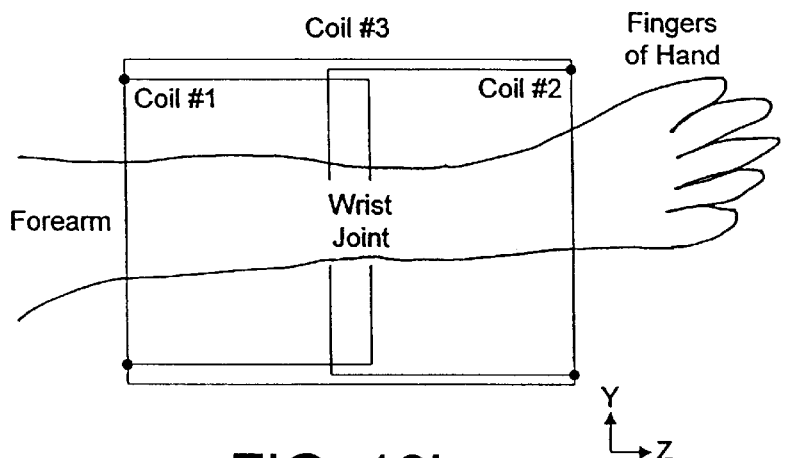
Figure 11A:
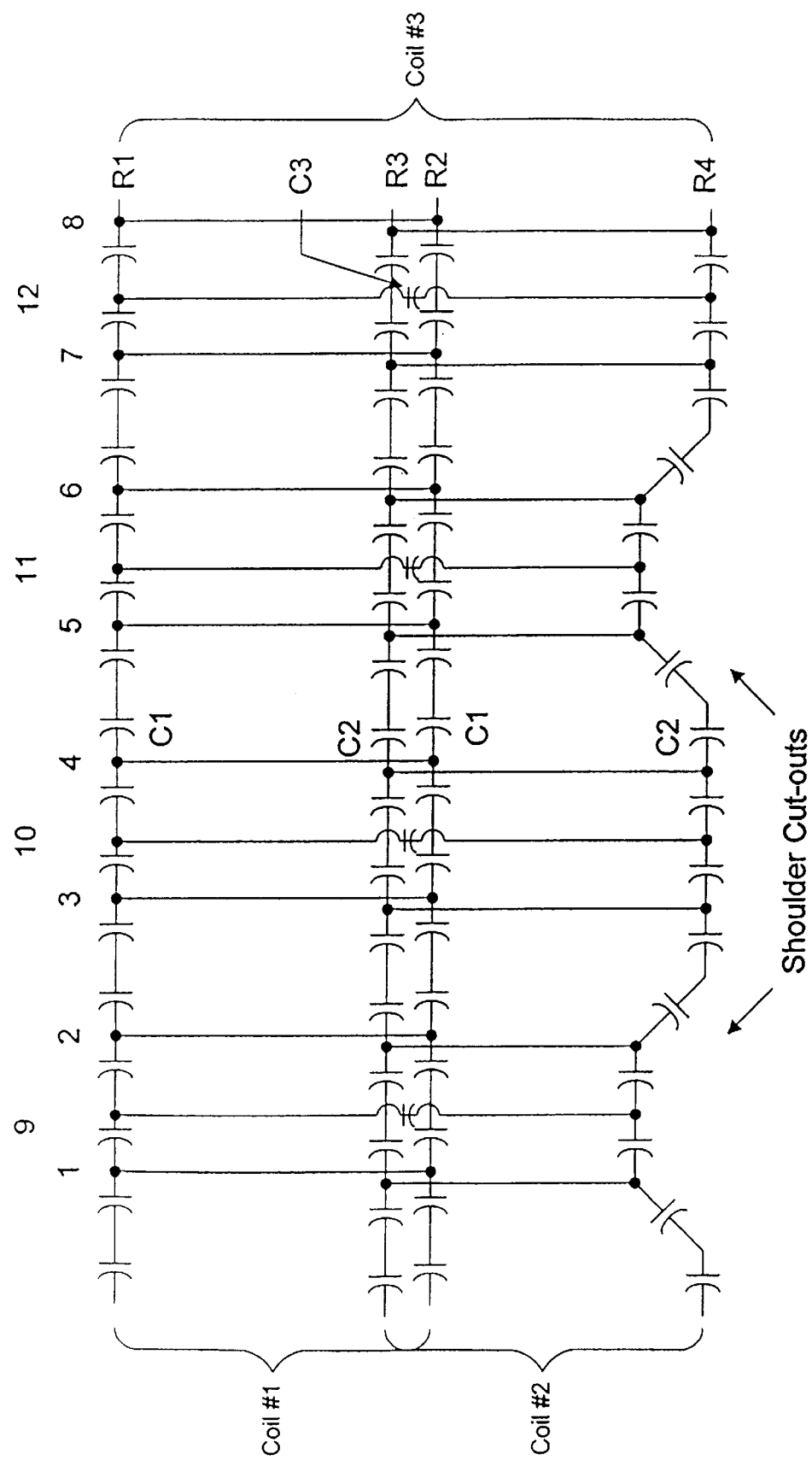
FIG. 11a is a planar schematic view of a 3-channel, quadrature head and neck array in accordance with the present invention.
Figure 11C:
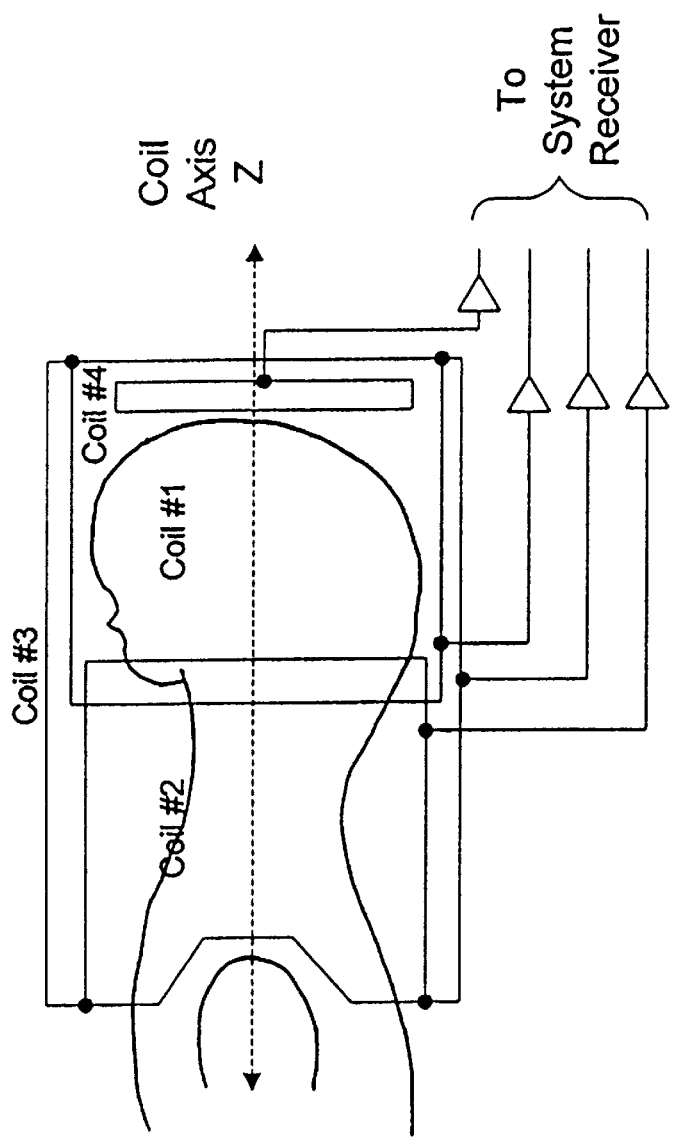
FIG. 11c is a modified coil of FIG. 11a including the addition of a fourth coil.
Figure 11B:
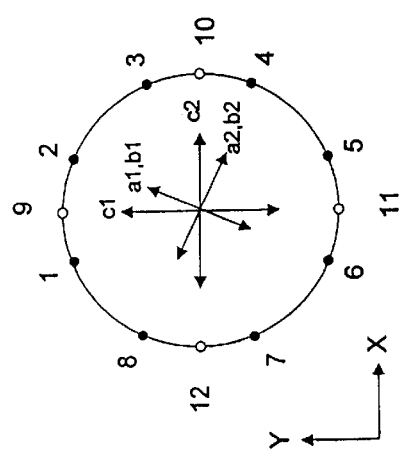

FIGS. 10a and 11b are front and side views of a 3 channel, quadrature wrist array. Coils #1 and #2 have 4 legs (1,2,3,4) and are overlapped for minimal mutual inductance. Coil #3 that connects coils #1 and #2 has four legs (5,6,7,8). Thus the entire wrist array has a total of 8 legs as shown in FIG. 10a. Please note, the opening of the wrist coil is elliptical in shape to accommodate imaging of the fingers of the human hand. This also facilitates lateral placement of the coil along side the patients body inside a MRI machine. This high S/N coil allows for high-resolution imaging of the carpal ligaments of the human wrist.

Embodiment #6—3 Channel, Quadrature Head and Neck Design

A planar schematic of the coil is shown in FIG. 11a. Coil #1 has 8 legs (1,2,3 ... 8) and covers the head FOV. Coil #2 has 8 legs (1,2,3 ... 8) and has shoulder cut outs to accomodate the entire human neck. Each of these coils are resonant at the NMR frequency. Coil #1 and #2 are overlapped for minimal mutual inductance. Coil #3 connects coil #1 and #2 at eight points and hence has 4 legs distributed at right angles from one another. Thus the entire head and neck coil has 12 legs. Here, coil #1 is resonant with C1, and coil #2 is resonant with C2 whereas coil #3 is resonant with C1, C2 and C3, respectively. A front view of the coil is shown in FIG. 11b.

Figure 3:
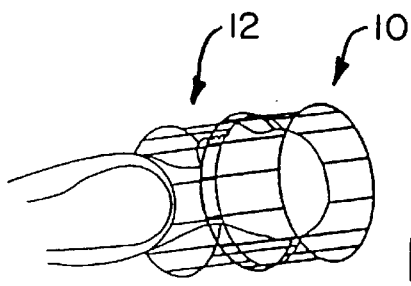
FIG. 3 is a perspective view of a quadrature, 2-channel birdcage array.
Figure 4A:
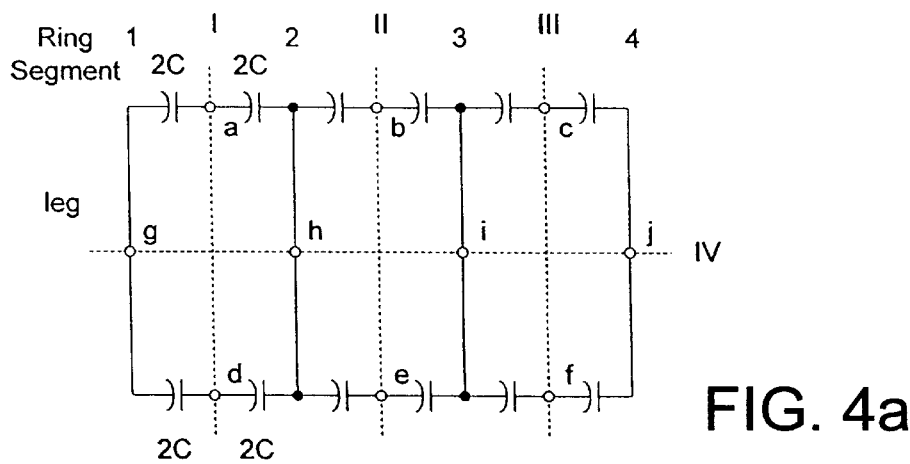
FIG. 4a is a schematic view of a distributed type surface coil.
Figure 4B:
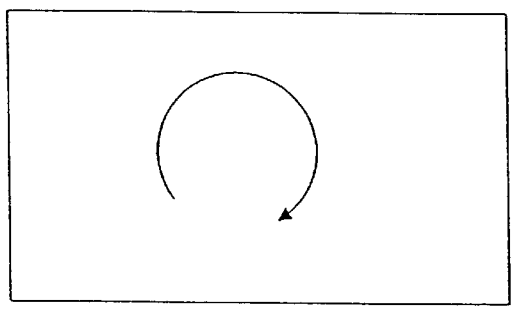
Figure 4C:
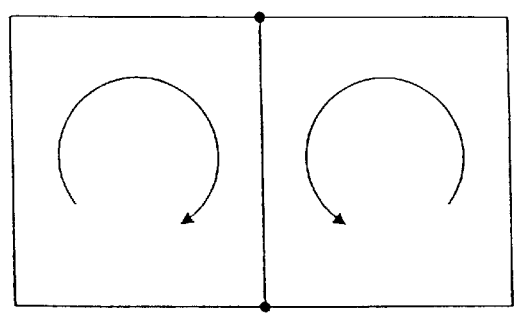
Figure 4D:
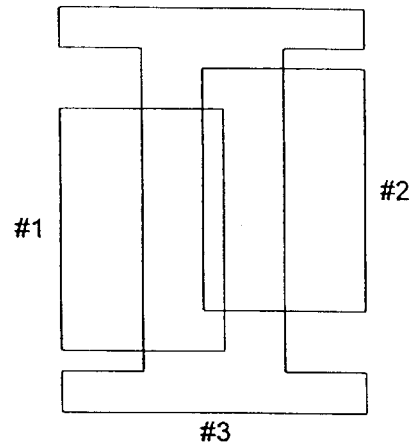
FIG. 4d represents a three coil arrangement of Boskamp et al.
Figure 5A:
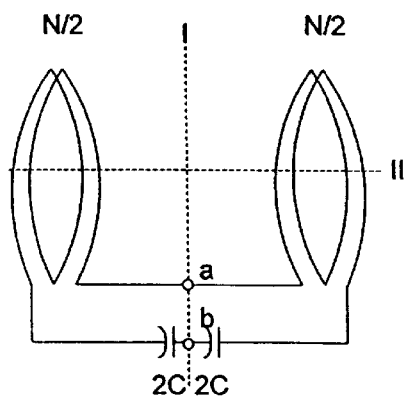
FIG. 5a represents schematically a solenoid head coil.
Figure 5B:
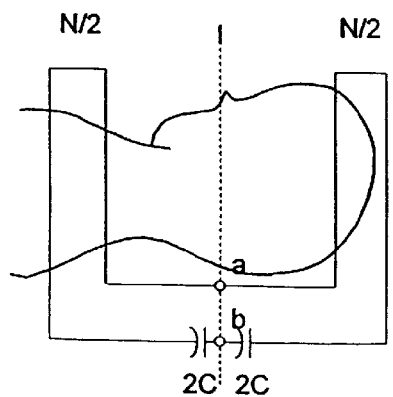
Figure 5C:
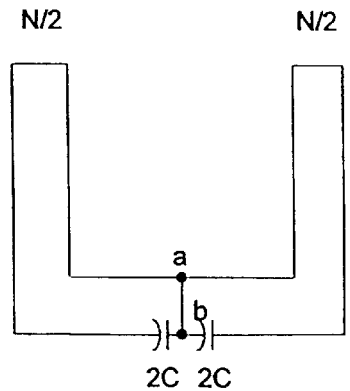
Figure 6:
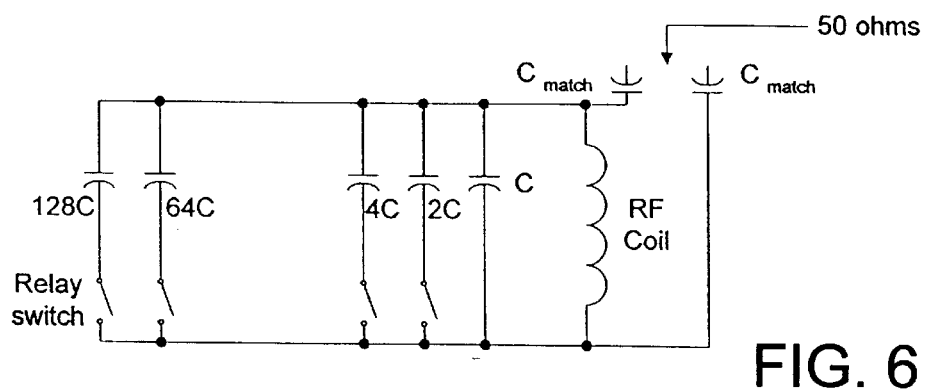
FIG. 6 is a schematic illustration of a single turn solenoid coil.

Here, just coil #1 or coil #2 can be turned ON for performing head or neck only studies. Also, all coils (#1, #2 & #3) can be turned ON to perform extended FOV head and neck studies, simultaneously. In this case where coil #3 spans a similar FOV as the combined FOVs of coils #1 & #2, the signals add up and since the noises are uncorrelated, enhanced S/N will be realized, unlike the prior art of FIG. 3. Also, coil #4 of FIG. 8d, can be added to the 3 channel, quadrature coil of FIG. 11 to further improve the S/N toward the top of the head (see FIG. 11c).

Embodiment #7—Distributed Surface Coil Array for Spine and Torso

Figure 12A:
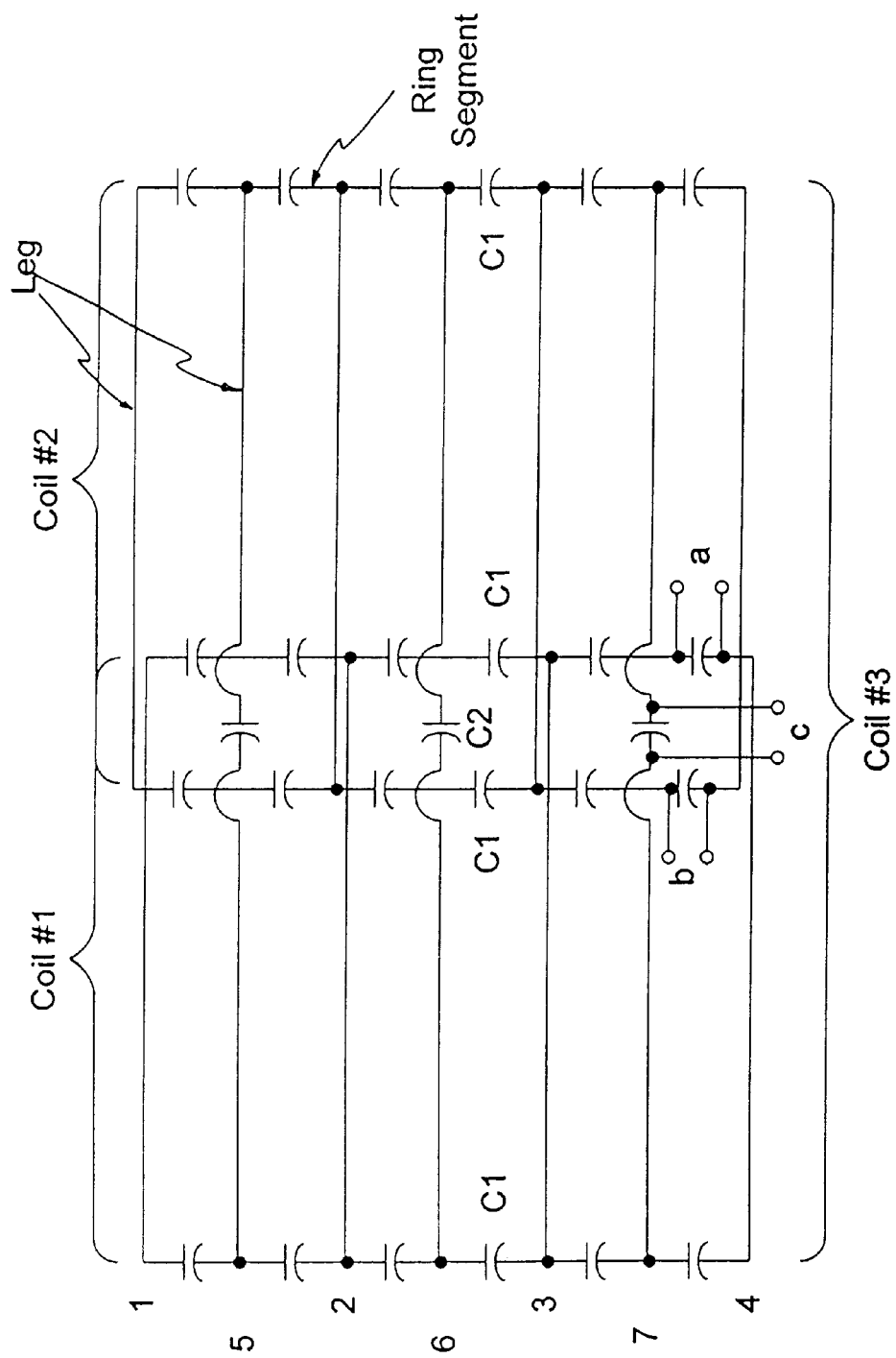
FIG. 12a is a schematic view of a distributed coil array for spine or torso imaging in accordance with the present invention.

FIG. 12a is a distributed surface coil array for brain of torso imaging. Here, coil #1 and #2 are overlapped to maintain minimum mutual inductance. Therefore, the net flux shared by these two coils is zero. Both these coils are identical in dimension. They comprise of 2 ring segments, 4 legs and are resonated with C1 value capacitors. These coils are matched to 50 ohms, across the terminals "a, b" similar to the circuit of FIG. 7e and interfaced to 2 channels of the MRI system. Evidently, these two outputs can be matched and summed using a phase shifter, resulting in a single channel quadrature output.

Coil #3 consists of 2 ring segments and 3 legs that connect to coils #1 and #2. Coil #3 is tuned to the resonance frequency of interest with C1 and C2 value capacitors. Coil #3 is matched to 50 ohms across "c" terminal using the similar circuitry of FIG. 7e. After the addition of coil #3, the isolation between coils #1 and #2 remained virtually the same, is indicative of a well isolated system. Please note, one integrated RF coil unit I comprises of coils #1, #2 and #3, respectively.

Figure 12B:
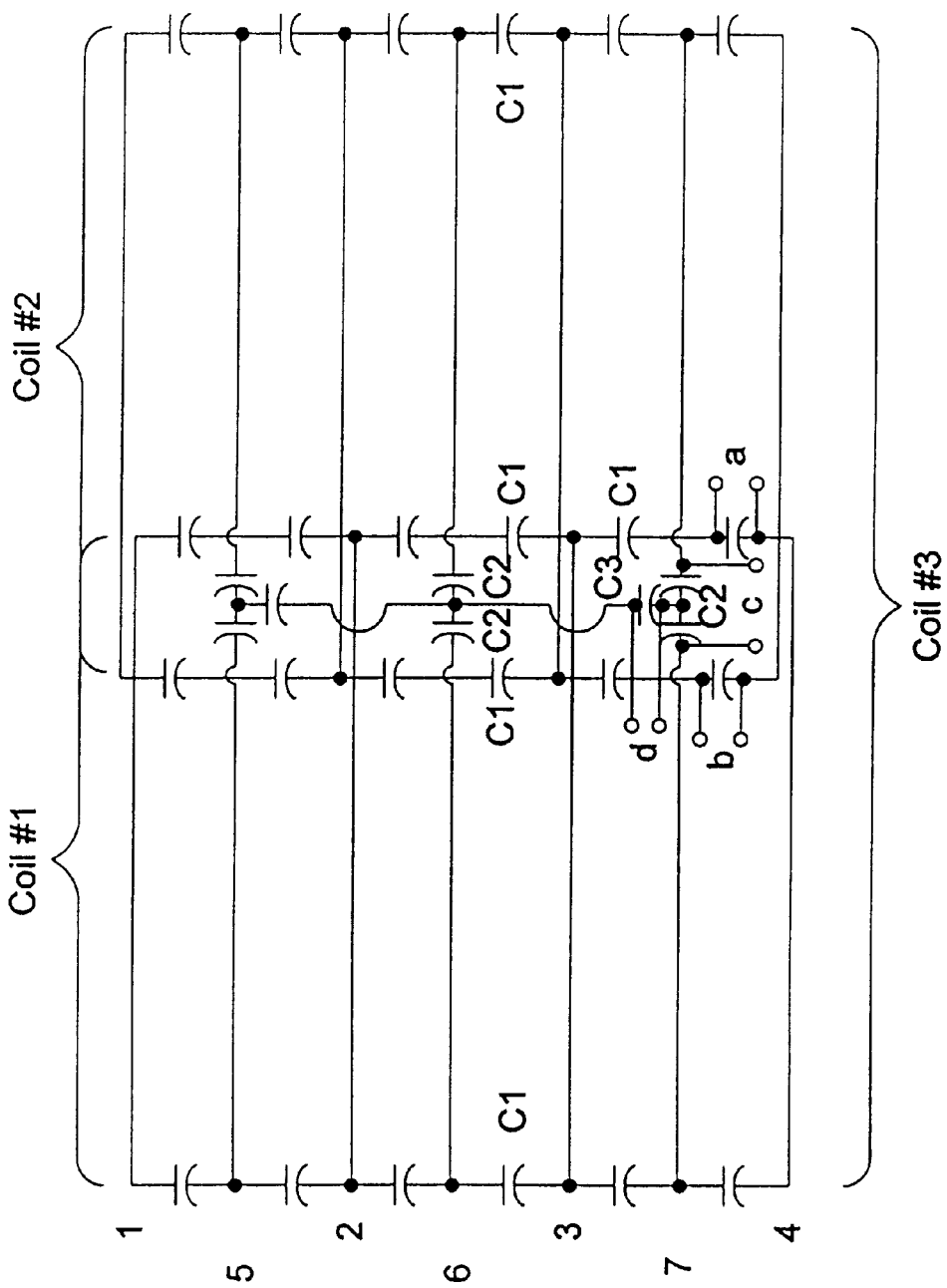
FIG. 12b is a schematic view of a modification of the coil array of FIG. 12a in which a fourth coil is formed.

FIG. 12b is an extension of FIG. 12a, where coil #3 has an additional ring segment resulting in coil #4 on the same coil system. This coil is tuned to the resonance frequency of interest with C1, C3 and C4. Coils #1 and #2 here are tuned with C1, whereas coil #3 is tuned with C1 and C3. The outputs "a, b" can either be routed to two receiver channels, or combined using a phase shifting network resulting in a single quadrature output. Similarly, the other two outputs, "c, d" can be either routed to two other receiver channels or combined prior to the receiver. Please note, one integrated RF coil unit I comprises of coils #1, #2, #3 and #4, respectively.

Figure 12C:
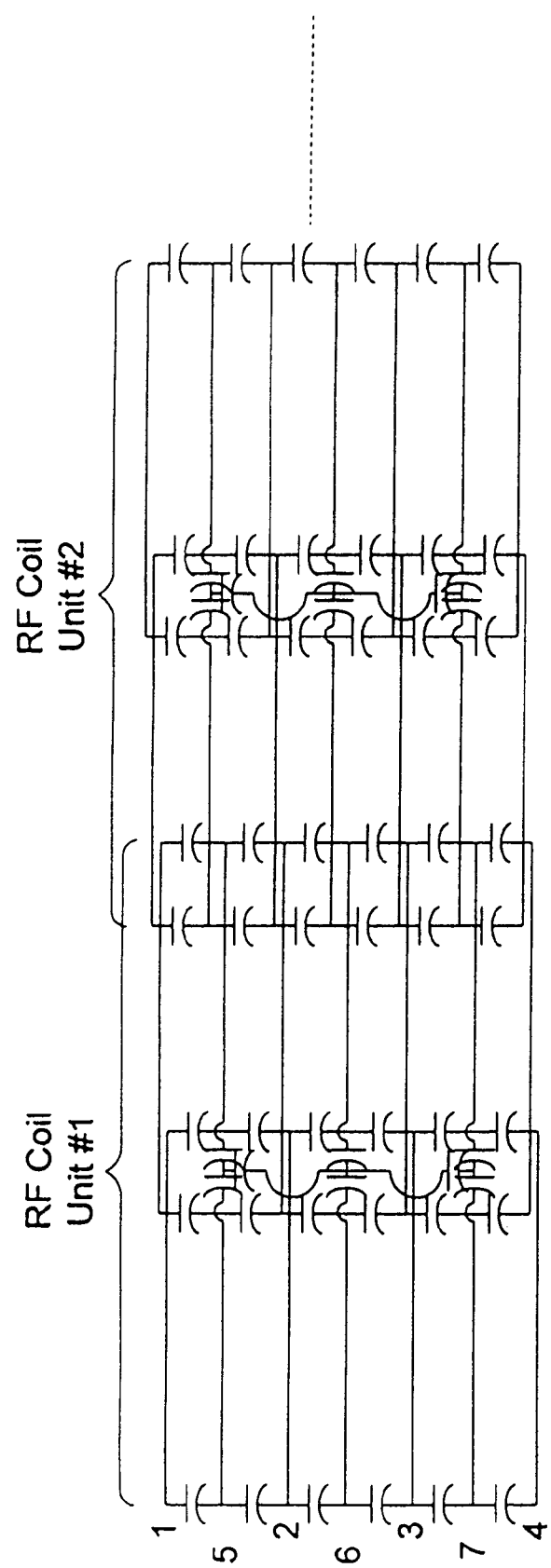
FIG. 12c is a schematic view of multiple arrays of FIGS. 12a or 12b integrated together in accordance with the present invention.

FIG. 12c is a result of many such integrated RF coil circuits I, II, ... of FIGS. 12a or 12b, in an array configuration. The coils of FIGS. 12 may be used to image the spine or wrapped around the human torso for imaging the liver, kidney, heart, etc. They may also be used to scan both feet for imaging the blood flow.

Embodiment #8—Solenoid Type Volume Coil

Figure 13A:
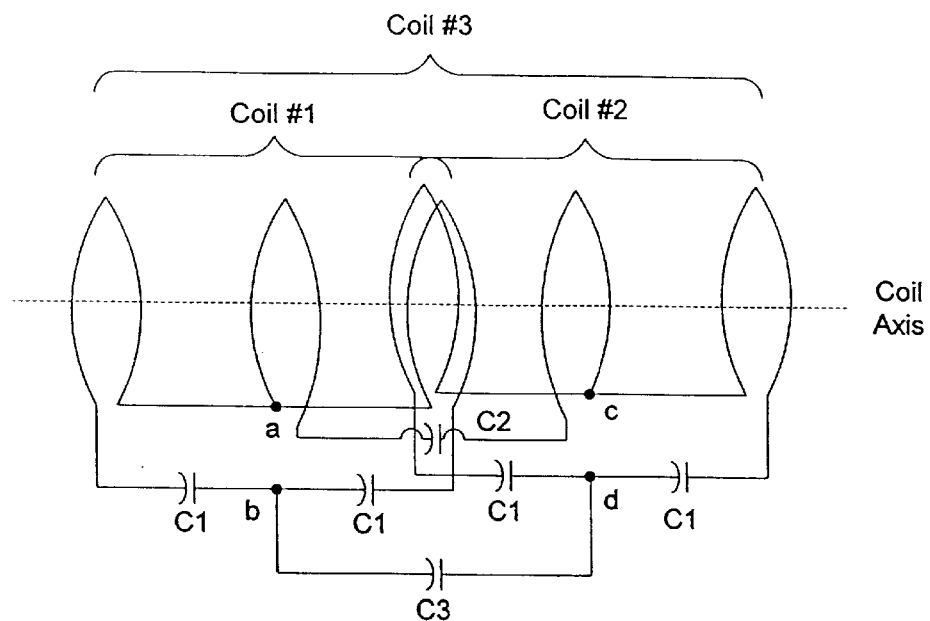
FIG. 13a is a schematic illustration of a solenoid type volume coil in accordance with the present invention.

The solenoid type volume coil of FIG. 13a has multiple uses. It can be used to image the human brain, knee, elbow, wrist, foot and ankle, torso in a vertical field NMR machine. This type of a coil may also be used in a NQR system and used to detect the explosives and narcotics in baggages, mails, etc. The NQR system may also be used as a security check at various public places, such as airports, railway stations,etc. and may be used to detect for plastic explosives, narcotics, etc.

FIG. 13a consists of a total of 3 solenoid coils. Coils #1 and #2 are identical in dimension. They both have 2 turns separated by a set distance and are tuned with C1 value capacitors. These coils are overlapped to maintain minimum mutual inductance, thus the net flux shared by these two coils are zero. Coil #3 is then introduced by shorting virtual ground points "a, b" in coil #1 to "c, d" in coil #2. However, the shorting between points "a, c" is done with two turns, the first turn exists in the virtual ground plane of coil #1 and the second turn in the virtual ground plane of coil #2. This is done such that coils #1 and #2 will not see coil #3. Also, this shorting is interrupted with C2 and the shorting between the points "b, d" is interrupted with C3 value capacitor. Please note, only two turns are used for coils #1 and #2, for simplicity. In practice, coils #1 and #2 may have N (N≧1) turns, and coil#3 may have M (M=N or M≠N) turns.

The resultant integrated structure I comprises of coils #1 and #2 that are overlapped for minimum mutual inductance and coil #3 physically connecting coils #1 and #2, such that there is no net coupling between coils #1 and #2 via coil #3. In this preferred case for human imaging, all coils are tuned to the same NMR frequency. However for the NQR case, all coils may be tuned to the same or different frequencies.

Figure 13B:
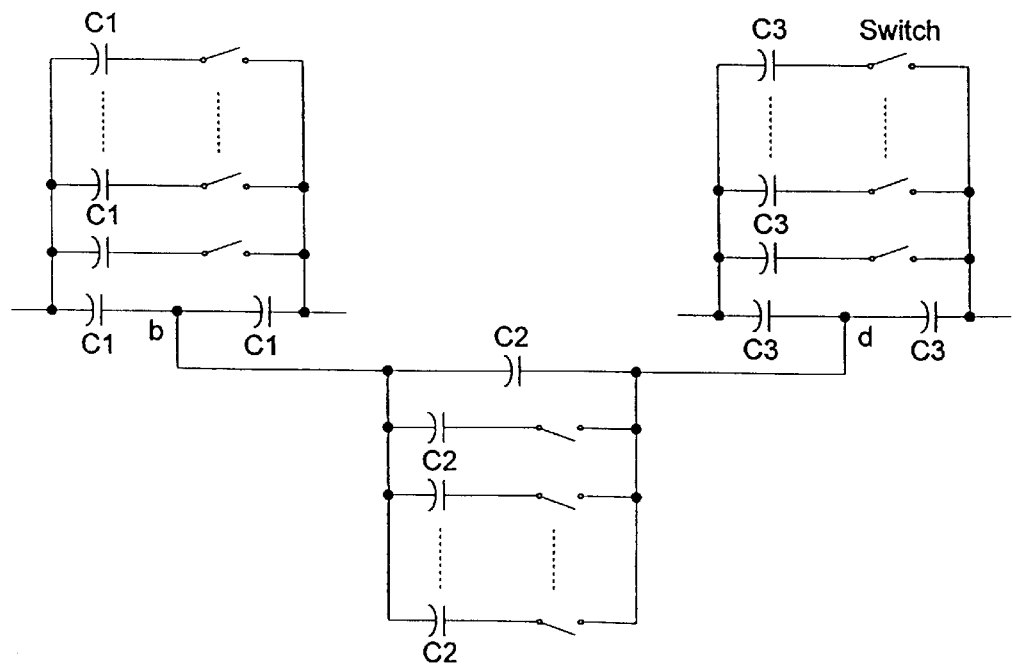
FIG. 13b is a schematic view of a preferred embodiment of the coil in FIG. 13a in accordance with the present invention.

A preferred embodiment is where all coils are tuned to different NQR frequencies and have their own tunable range of frequencies, lets say for example coil #1 covers from 0.5–1.5 MHz, coil #2 from 1.5–3.0 MHz and coil #3 from 3–5 MHz, respectively. Each coil design is optimized to cover this frequency range and has its own capacitor bank as shown in FIG. 13b to tune the specified frequency range. The individual switches may be computer controlled (not shown) to tune the individual RF coil to the specified resonance frequencies. The object that need to be scanned is introduced along the coil axis.

Alternately, the solenoid design may be adapted to a surface type design and may be used for surface detection of drugs, narcotics, explosives, etc. The RF coil may also be used in a quasi surface—volume type design as well, for several medical and non-medical applications.

Figure 14:
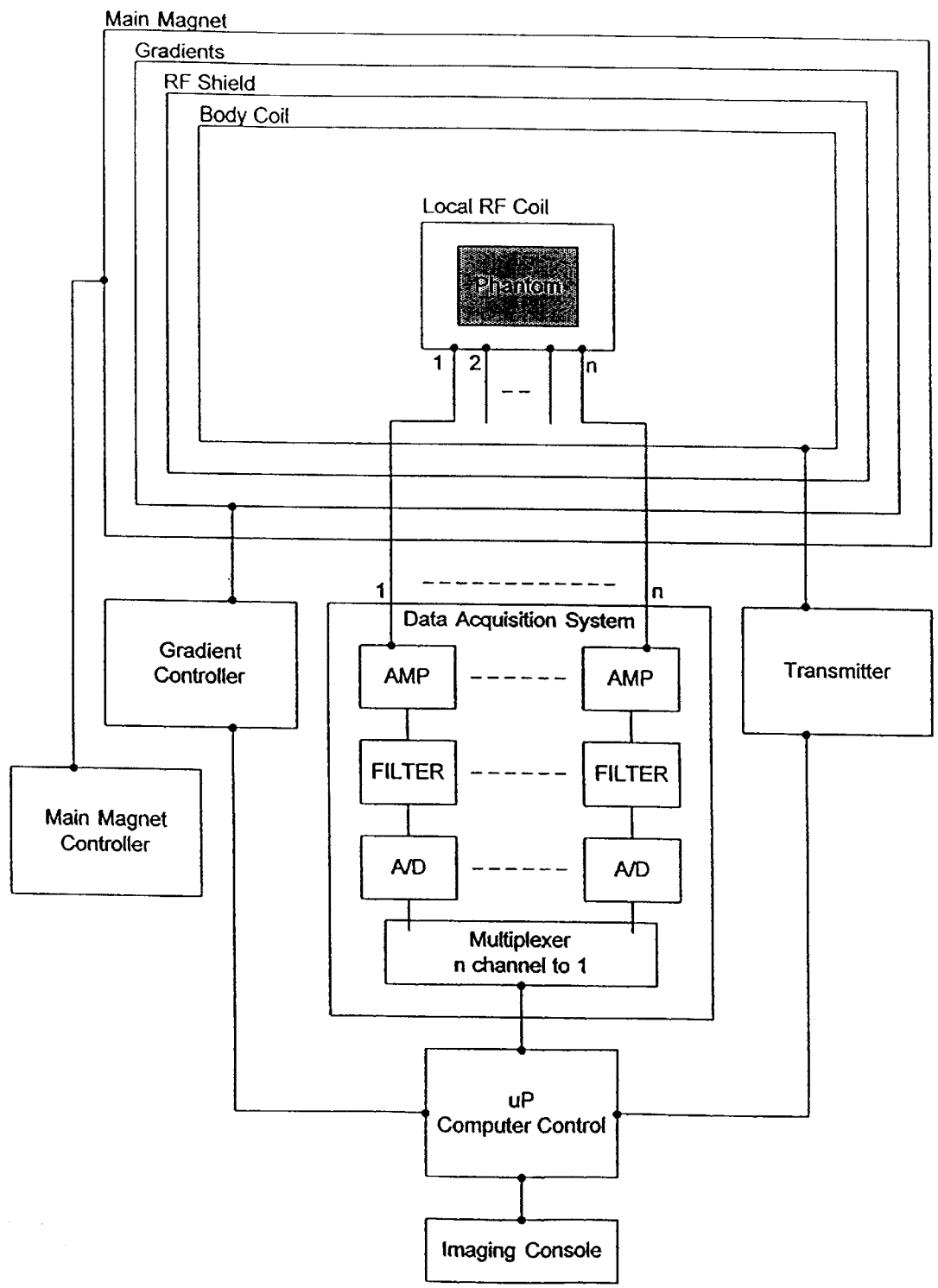
FIG. 14 is a block diagram of a system incorporating an coil in accordance with the present invention.

FIG. 14 is a system block diagram, which illustrates the utility of the RF coil of the pressent invention in NMR imaging and spectroscopy, for example. The system has a main magnet which covers the time varying gradient coils, an RF shield that isolates the RF coil from the gradient coils and a whole-body RF coil most commonly used for uniform B field transmit over a large imaging FOV. The main magnet strength sets the NMR frequency of operation. The time varying gradient fields help spatially encode the NMR signals. The RF whole body coil is used to transmit, while the local RF coil is used to pick up the NMR signals from the object under investigation (NMR phantom). A number of receiver coils may be used in an array configuration and may be summed either analog or digitally to produce the resultant image. Signals from the several receiver ports may be acquired via one or multiple receiver channels. An n-to-1 channel multiplexer is shown in the drawing. This helps by-pass n channel coil data to use one channel of the NMR system. Alternatively, an n channel NMR system may also be used.

Similarly, a NQR system may be realized but without the main magnet of FIG. 14. The resonance frequencies are set by the different nuclei themselves. Thus there is no need for the main magnet of FIG. 14. The time varying gradients of FIG. 14 may or may not be used, depending on the technique used to map the chemical species.

From all the above description, for someone skilled in the art, is must now be apparent that the inventive novel concept of FIG. 7 may be adapted to a number of different coil designs for the several resonance techniques, such as NMR, NQR, etc. It must also now be apparent that the individual coils in an integrated RF coil system may be tuned to the same or different frequencies.

It is to be noted that the individual coils in the array may be shaped in such a way to provide a high S/N and uniform coverage over the imaging FOV. The coils may be used to image in the different operating modes. The signal may be combined prior to the preamplifier or post the preamplifier in analog or digital fashion. The individual coils in the array may be tuned to one or more frequencies.

It must be further apparent that the coil designs in the distributed cases may be of the low-pass, high-pass, band-pass, band-stop or a combination of the above different configurations. Also, the coils may be of the volume type, surface type or a combination of both. Individual coils in the array may be linear or in quadrature. The coils may be used for transmit only, receive only or may be used for transmit and receive purposes. Individual coils in the array may be interfaced to separate channels in the multi-channel resonance system or may be time-multiplexed to one or more channels of a single or multi-channel resonance system.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A radio-frequency (RF) coil array for resonance imaging/analysis, comprising:
    a first RF coil sensitive to RF signals produced during resonance imaging/analysis;
    a second RF coil located relative to the first RF coil with substantially no net coupling therebetween at a frequency or frequencies of the RF signals; and
    a third RF coil electrically connected and located relative to the first RF coil and the second RF coil such that there is substantially zero net current flow between the first RF coil and the second RF coil via the third RF coil, each of the first RF coil, second RF coil and third RF coil being substantially isolated from the other coils at the frequency or frequencies of the RF signals.

2. The coil array of claim 1, wherein the first RF coil, second RF coil and third RF coil are sufficiently isolated from one another to maintain predefined current distributions and mode orientations for the respective coils.

3. The coil array of claim 1, wherein the third RF coil has a field-of-view which is similar as compared to a combined field-of-view of the first RF coil and the second RF coil.

4. The coil array of claim 1, wherein each of the first RF coil, second RF coil and third RF coil are volume type coils.

5. The coil array of claim 4, wherein each of the first RF coil, second RF coil and third RF coil are birdcage type coils.

6. The coil array of claim 5, wherein the coil array is sized to receive at least one of a human head, a human knee, and a human wrist within the first RF coil second RF coil and third RF coil.

7. The coil array of claim 5, further comprising a fourth RF coil positioned toward an end of the coil array.

8. The coil array of claim 5, wherein the coil array is sized to receive a human head.

9. The coil array of claim 5, wherein the coil array is sized to receive a human head and neck.

10. The coil array of claim 4, wherein each of the first RF coil, second RF coil and third RF coil are solenoid type coils.

11. The coil array of claim 10, wherein the coil array is sized to receive at least one of a human head, knee, wrist or torso within the first RF coil, second RF coil and third RF coil.

12. The coil array of claim 1, wherein each of the first RF coil, second RF coil and third RF coil are surface type coils.

13. The coil array of claim 12, further comprising a fourth RF coil.

14. The coil array of claim 1, wherein the net shared magnetic flux between the first RF coil and the second RF coil is substantially zero.

15. The coil array of claim 1, wherein the third RF coil is physically connected to the first RF coil and the second RF coil.

16. The coil array of claim 1, wherein the first RF coil and the second RF coil maintain substantially similar physical dimensions.

17. The coil array of claim 1, wherein each of the first RF coil, second RF coil and third RF coil is configured to provide a quadrature output.

18. The coil array of claim 1, further comprising means for selectively turning the first RF coil, second RF coil and third RF coil on and off to control a mode of operation.

19. The coil array of claim 1, wherein at least one of the first RF coil, second RF coil and third RF coil is a volume type coil, and at least another of the first RF coil, second RF coil and third RF coil is a surface type coil.

20. The coil array of claim 1, wherein the first RF coil, second RF coil and third RF coil are tuned to the same resonance frequency.

21. The coil array of claim 1, wherein the first RF coil and the second RF coil are tuned to one resonance frequency, and the third RF coil is tuned to another resonance frequency.

22. The coil array of claim 1, wherein the first RF coil, second RF coil and third RF coil are tuned to respective different resonance frequencies.

23. A system comprising the coil array of claim 1, and further comprising means for driving the coil array during imaging/analysis.

24. A resonance imaging/analysis system, comprising:
    an RF coil as recited in claim 1; and
    means for processing RF signals which are at least one of received from the RF coil and transmitted from the RF coil in order to obtain a resonance image/analysis.

25. The coil array of claim 1, wherein the isolation between the first and second RF coils is substantially the same with the third RF coil as without the third RF coil.

26. A radio-frequency (RF) coil array for resonance imaging/analysis, comprising:
    a first RF coil sensitive to RF signals produced during resonance imaging/analysis;
    a second RF coil located relative to the first RF coil with substantially no net coupling therebetween at a frequency or frequencies of the RF signals; and
    a third RF coil electrically connected and located relative to the first RF coil and the second RF coil such that there is substantially no net coupling between the first RF coil and the second RF coil via the third RF coil, each of the first RF coil, second RF coil and third RF coil being substantially isolated from the other coils at the frequency or frequencies of the RF signals.

27. The coil array of claim 26, wherein the isolation between the first and second RF coils is substantially the same with the third RF coil as without the third RF coil.

28. A radio-frequency (RF) coil array for resonance imaging/analysis, comprising:

a first RF coil sensitive to RF signals produced during resonance imaging/analysis;

a second RF coil located relative to the first RF coil with substantially no net coupling therebetween at a frequency or frequencies of the RF signals; and a third RF coil located relative to the first RF coil and the second RF coil such that each of the first RF coil, second RF coil and third RF coil are substantially isolated from the other coils at the frequency or frequencies of the RF signals;

wherein a field-of-view of the third RF coil substantially overlaps and is substantially similar to a combined field-of-view of the first and second RF coils.

29. The coil array of claim 28, wherein the third RF coil is electrically connected to the first RF coil and the second RF coil.

30. The coil array of claim 28, wherein the third RF coil is electrically connected to the first and second RF coils, and the isolation between the first and second RF coils is substantially the same with the third RF coil as without the third RF coil.

31. The coil array of claim 30, wherein the third RF coil is electrically connected to the first RF coil and the second RF coil.

32. A radio-frequency (RF) coil array for resonance imaging/analysis, comprising:

a first RF coil sensitive to RF signals produced during resonance imaging/analysis;

a second RF coil located relative to the first RF coil with substantially no net coupling therebetween at a frequency or frequencies of the RF signals; and a third RF coil located relative to the first RF coil and the second RF coil such that there is substantially no net coupling between the first RF coil and the second RF coil via the third RF coil, each of the first RF coil, second RF coil and third RF coil being substantially isolated from the other coils at the frequency or frequencies of the RF signals;

wherein a field-of-view of the third RF coil substantially overlaps and is substantially similar or larger than a combined field-of-view of the first and second RF coils.

33. The coil array of claim 32, wherein the third RF coil is electrically connected to the first and second RF coils, and the isolation between the first and second RF coils is substantially the same with the third RF coil as without the third RF coil.

* * * * *